(12) United States Patent
Dumesic et al.

(10) Patent No.: US 10,137,434 B2
(45) Date of Patent: Nov. 27, 2018

(54) METHOD TO STABILIZE BASE METAL CATALYSTS BY OVERCOATING VIA ATOMIC LAYER DEPOSITION AND RESULTING PRODUCT

(71) Applicant: Wisconsin Alumni Research Foundation, Madison, WI (US)

(72) Inventors: James A. Dumesic, Verona, WI (US); Brandon J. O'Neill, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 84 days.

(21) Appl. No.: 15/232,910

(22) Filed: Aug. 10, 2016

(65) Prior Publication Data
US 2016/0361708 A1 Dec. 15, 2016

Related U.S. Application Data

(62) Division of application No. 13/790,722, filed on Mar. 8, 2013.

(51) Int. Cl.
*B01J 33/00* (2006.01)
*B01J 23/72* (2006.01)
(Continued)

(52) U.S. Cl.
CPC .............. *B01J 23/72* (2013.01); *B01J 21/04* (2013.01); *B01J 21/063* (2013.01); *B01J 23/94* (2013.01); *B01J 33/00* (2013.01); *B01J 35/0006* (2013.01); *B01J 35/02* (2013.01); *B01J 37/0221* (2013.01); *B01J 37/08* (2013.01); *C07D 307/44* (2013.01); *Y02P 20/584* (2015.11)

(58) Field of Classification Search
None
See application file for complete search history.

(56) References Cited

U.S. PATENT DOCUMENTS

| | | |
|---|---|---|
| 6,270,572 B1 | 8/2001 | Kim et al. |
| 6,287,965 B1 | 9/2001 | Kang et al. |
| | (Continued) | |

OTHER PUBLICATIONS

Ge et al (Core-Satellite Nanocomposite Catalysts Protected by a Porous Shell: Controllable Reactivity, High Stability, and Magnetic Recyclability, Angew Chem Int Ed (2008) 47, 8924-8928).*

(Continued)

*Primary Examiner* — Melvin C. Mayes
*Assistant Examiner* — Michael Forrest
(74) *Attorney, Agent, or Firm* — Joseph T. Leone, Esq.; DeWitt Ross & Stevens S.C.

(57) ABSTRACT

A method for stabilizing a metal or metal-containing particle supported on a surface is described, along with the resulting composition of matter. The method includes the steps of depositing upon the surface a protective thin film of a material of sufficient thickness to overcoat the metal or metal-containing particle and the surface, thereby yielding an armored surface; and then calcining the armored surface for a time and at a temperature sufficient to form channels in the protective thin film, wherein the channels so formed expose a portion of the metal- or metal-containing particle to the surrounding environment. Also described is a method of performing a heterogeneous catalytic reaction using the stabilized, supported catalyst.

11 Claims, 16 Drawing Sheets

(51) Int. Cl.
- B01J 37/08 (2006.01)
- B01J 35/00 (2006.01)
- B01J 35/02 (2006.01)
- B01J 23/94 (2006.01)
- B01J 21/06 (2006.01)
- B01J 21/04 (2006.01)
- B01J 37/02 (2006.01)
- C07D 307/44 (2006.01)

(56) References Cited

U.S. PATENT DOCUMENTS

2002/0055664 A1  5/2002  Lu
2014/0094635 A1  4/2014  Lu et al.

OTHER PUBLICATIONS

Abdulagatov et al., Al2O3 and TiO2 Atomic Layer Deposition on Copper for Water Corrosion Resistance. *ACS Applied Materials & Interfaces* 3, 4593-4601 (2011).

Besson et al., Deactivation of metal catalysts in liquid phase organic reactions. *Catalysis Today* 81, 547-559 (2003).

*Catalysis without Precious Metals.* (Wiley-VCH Verlag GmbH & Co. KGaA, 2010) (Book)

Chinchen et al., The measurement of copper surface areas by reactive frontal chromatography. *Journal of Catalysis*, 103, 79-86 (1987).

George, S.M. (2010). "Atomic Layer Deposition: An Overview". *Chem. Rev.* 110 (1): 111-131.

Greeley, J., Structural effects on trends in the deposition and dissolution of metal-supported metal adstructures. *Electrochimica Acta*, 55, 5545-5550 (2010).

Hagaman et al., Surface alumina species on modified titanium dioxide: A solid-state 27Al MAS and 3QMAS NMR investigation of catalyst supports. *Solid State Nuclear Magnetic Resonance* 37, 82-90 (2010).

"Handbook of Thin Film Materials", a five-volume set published Oct. 15, 2001, by Academic Press of San Diego, California, ISBN:0125129084. Chapter 2 of vol. 1 is titled "Atomic Layer Deposition," and was authored by Mikko Ritala and Markku Leskela.

Horne et al., Foldamers with Heterogeneous Backbones, Accounts of Chemical Research, vol. 41, No. 10, 1399-1408 (2008).

Kim, et al., CO—NO and CO—O2 Interactions on Cu(100) between 25 and 200 K Studied with Infrared Reflection Absorption Spectroscopy. *The Journal of Physical Chemistry* B 109, 1891-1895 (2005).

Liang et al., Stabilization of Supported Metal Nanoparticles Using an Ultrathin Porous Shell. *ACS Catalysis* 1, 1162-1165 (2011).

Lu et al., Porous Alumina Protective Coatings on Palladium Nanoparticles by Self-Poisoned Atomic Layer Deposition. *Chemistry of Materials* 24, 2047-2055 (2012).

Lu et al., Coking- and Sintering-Resistant Palladium Catalysts Achieved Through Atomic Layer Deposition. *Science* 335, 1205-1208 (Feb. 2012).

Miikkulainen et al., "Crystallinity of inorganic films grown by atomic layer deposition: Overview and general trends," J. Appl. Phys. 113:021301-021301-101 (2013).

Puurunen, R.L., Surface chemistry of atomic layer deposition: A case study for the trimethylaluminum/water process. *Journal of Applied Physics* 97, 121301-121301-52 (2005).

Skinner et al., Joint diffraction and modeling approach to the structure of liquid alumina. *Physical Review B* 87, 024201-024201-16 (2013).

Ritala et al., "Handbook of Thin Film Materials", a five-volume set published Oct. 15, 2001, by Academic Press of San Diego, California, ISBN:0125129084. Chapter 2 of vol. 1 is titled "Atomic Layer Deposition", 103-159.

Sun et al., Chemisorption of hydrogen on stepped (410) surfaces of Ni and Cu. *Surface Science* 338, 11-18 (1995).

Twigg et al., Deactivation of supported copper metal catalysts for hydrogenation reactions. *Applied Catalysis A: General* 212, 161-174 (2001).

Twigg et al., Deactivation of Copper Metal Catalysts for Methanol Decomposition, Methanol Steam Reforming and Methanol Synthesis. *Topics in Catalysis* 22, 191-203 (2003).

Venkov et al., FTIR study of CO interaction with Cu/TiO2. *Catalysis Communications* 4, 209-213 (2003).

Zeitsch, K.J., *The chemistry and technology of furfural and its many by-products.* Sugar Series (Elsevier, Amsterdam, Netherlands, (2000), vol. 13 (Book).

* cited by examiner

METHOD TO STABILIZE BASE METAL CATALYSTS BY OVERCOATING VIA ATOMIC LAYER DEPOSITION AND RESULTING PRODUCT

CROSS-REFERENCE TO RELATED APPLICATIONS

This is a divisional of application Ser. No. 13/790,722, filed Mar. 8, 2013, now abandoned.

FEDERAL FUNDING STATEMENT

This invention was made with government support under DE-AC02-06CH11357 awarded by the US Department of Energy. The government has certain rights in the invention.

BACKGROUND

Precious metal catalysts are used extensively in the petrochemical industry. Because of their functionality, precious metal catalysts are also likely to play a significant role in future bio-refineries. The main drawback of these catalysts, of course, is their very high price. For example, the spot price for gold crested $1000/ounce in September 2009, passed $1500/ounce in March of 2010, and as of February 2013 is trading at approximately $1600/ounce. Silver and platinum prices have experienced similar increases and as of February 2013 are trading near their all-time highs. While it would be desirable to replace these precious metal catalysts with more abundant base metals such as copper, nickel, or iron, these base metal catalysts are subject to deactivation by leaching and sintering under condensed-phase reaction conditions. (1-4)

Atomic layer deposition (ALD) is a self-limiting, sequential surface chemistry that deposits a conformal, thin-film of material onto a substrate, even on substrates having high aspect ratios. ("Conformal" in the context of ALD means that the thin film deposited by ALD has a substantially uniform thickness everywhere along the coated substrate.) ALD enables the deposition of atomic-scale thin-films of controlled thickness. ALD is similar in chemistry to chemical vapor deposition (CVD), but separates the deposition reaction into two half-reactions that are performed separately from one another. In this fashion, the thickness of the deposited film can be very accurately controlled. See, for example, Steven M. George (2010). "Atomic Layer Deposition: An Overview". *Chem. Rev.* 110 (1): 111-131.

Chemical vapor deposition (CVD) refers to a series of closely-related processes in which a substrate is exposed to one or more volatile precursors which react with and/or decompose on the substrate surface to produce a conformal thin film. As noted, CVD is practiced in a wide variety of formats, all of which share the same basic feature of bringing the volatile precursors into contact with a substrate to deposit an atomically thin layer of a desired material. The various types of CVD can be classified in various ways, such as by the operating pressure of the process or by the means by which the chemical reactions are initiated to form the thin film on the substrate. Thus, there are known in the art atmospheric pressure CVD (APCVD), low-pressure CVD (LPCVD) (CVD at sub-atmospheric pressures; reduced pressures tend to reduce unwanted gas-phase reactions and improve film uniformity), and uiltrahigh vacuum CVD (UHVCVD) (CVD at very low pressure, typically below $10^{-6}$ Pa). CVD may also be classified by the physical characteristics of reactive vapor. Thus, known to the art are CVD processes including aerosol-assisted CVD (AACVD). Here, the precursors are transported to the substrate by means of a liquid/gas aerosol. AACVD is suitable for use with non-volatile precursors. In direct liquid injection CVD (DLICVD) the precursors are in liquid form (liquid or solid dissolved in a convenient solvent) and injected in a vaporization chamber and then transported to the substrate. High growth rates can be reached using DLICVD. CVD methods may also be characterized by how the plasma vapor is formed or maintained. Thus, known to the art are various types of CVD such as microwave plasma-assisted CVD (MPCVD) and plasma-enhanced CVD (PECVD). PECVD utilizes plasma to enhance chemical reaction rates of the precursors and also allows deposition of the thin film at lower temperatures, which could be critical for temperature-sensitive materials. Remote plasma-enhanced CVD (RPECVD) is similar to PECVD except that the substrate is not directly in the plasma discharge region. Removing the substrate from the plasma region allows processing temperatures to drop even further, even down to room temperature with certain thin films. Atomic layer CVD (ALCVD) enables depositing successive layers of different substances to produce layered, crystalline films. ALCVD is also known as atomic layer epitaxy.

Combustion Chemical Vapor Deposition (CCVD) is an open-atmosphere, flame-based technique for depositing high-quality thin films and nanomaterials. Hot wire CVD (HWCVD), also known as catalytic CVD (Cat-CVD) or hot filament CVD (HFCVD), uses a hot filament to chemically decompose the source gases which are then contacted with the substrate to be coated. Hybrid Physical-Chemical Vapor Deposition (HPCVD)—involves both chemical decomposition of a precursor gas and vaporization of a solid source to yield a reactive vapor that then forms the coating on the substrate. Metalo-organic chemical vapor deposition (MOCVD) is based on metalo-organic precursors. Rapid thermal CVD (RTCVD) uses heating lamps or other means to heat the substrate very rapidly. Heating only the substrate rather than the reactive gas or chamber walls helps reduce unwanted gas-phase reactions that can lead to particle formation.

Coking- and sintering-resistant palladium catalysts have been described for use in gas-phase heterogeneous reactions. (14) Here, the authors noted that overcoating of supported metal nanoparticles effectively reduced deactivation and coking in high-temperature, gas-phase applications of heterogeneous catalysts. In this paper, a palladium catalyst was overcoated with 45 layers of alumina via ALD. The coated catalysts were then used for 1 hour in oxidative dehydrogenation of ethane to ethylene at 650° C. Coking of the coated palladium catalyst was greatly reduced. Scanning transmission electron microscopy revealed that the morphology of the coated catalyst was not changed after the ethane dehydrogenation reaction was run at 675° C. for 28 hours. Coating the palladium catalyst with alumna improved the yield of ethylene as compared to the non-coated catalyst. The reactions described in this work are gas-phase only, and used only palladium catalysts (a noble metal catalyst). Using a base metal catalyst in condensed-phase conditions is significantly different from using noble metals in either the gas phase or condensed phase due to the possibility of leaching.

SUMMARY OF THE INVENTION

Disclosed herein are methods for stabilizing a metal or metal-containing particle supported on a surface, methods for using the stabilized metal or metal-containing particles in heterogeneous catalytic reactions, and the resulting stabilized composition of matter. The method comprises depositing upon the surface by atomic layer deposition, (ALD), chemical vapor deposition (CVD), or any other suitable thin film-forming methodology (such as, but not limited to, molecular beam epitaxy, thermal evaporation, sputtering, pulsed laser deposition, cathodic arc deposition, electrohydrodynamic deposition, etc.), a protective thin film of a material of sufficient thickness to overcoat the metal or metal-containing particle and the surface, thereby yielding an armored surface. The armored surface is then calcined for a time and at a temperature sufficient to form channels in the protective thin film, wherein the channels so formed expose a portion of the metal- or metal-containing particle to the surrounding environment.

The method may comprise depositing by ALD, CVD, or any other method, any material capable of being deposited at atomic thicknesses in one or more layers (e.g., about 1 nm to about 100 nm). (For an excellent review of the ALD process, see Miikkulainen et al. (2013) "Crystallinity of inorganic films grown by atomic layer deposition: Overview and general trends," J. Appl. Phys. 113:021301, incorporated herein by reference). A very wide range of materials can be deposited by ALD, CVD, and other thin film-forming methods and thus can be used in the present method, including (without limitation metal oxides, metal nitrides, metal chalcogenides, carbides, phosphides, arsenides, sulfides, selenides, tellurides, fluorides, metals, etc. See FIG. 10, which is a depiction of the periodic table of elements that provides an overview of the materials to date that have been fabricated by ALD. (Taken from Miikkulainen et al., supra.) All of the materials referenced in FIG. 10 may be used in the present method. These same materials can also be deposited by CVD. In all versions of the method and compositions of matter disclosed herein, the material deposited by ALD may be a material selected from the group consisting of $AlO_x$, $HfO_x$, $HfSiO_x$, $LaO_x$, $SiO_x$, STO, $TaO_x$, $TiO_x$, $ZnO_x$, $ZrO_x$, $WO_x$, $CeO_x$, $MgO_x$, $AlN_x$, $HfN_x$, $SiN_x$, $TaN_x$, $TiN_x$, $AlC_x$, $ZrC_x$, $TiC_x$, $WC_x$, $CeC_x$, and $MgC_x$, wherein subscript "x" is a real, rational number greater than zero. Likewise, in all versions of the method and compositions of matter disclosed herein, the metal or metal-containing particle may comprise any metal of any description, including a base metal and/or a noble metal, or a combination of base and noble metals. The metal or metal-containing particle may comprise one metal or more than one metal. The metal or metal-containing particle may, for example, comprise a metal selected from the group consisting of iron (Fe), nickel (Ni), copper (Cu), zinc (Zn), and lead (Pb).

The protective thin film may be deposited via about 20 to about 200 cycles of ALD or via about 25 to about 100 cycles of ALD or via about 25 to about 75 cycles of ALD. Using a number of ALD cycles above and/or below these two ranges is explicitly within the scope of this disclosure.

In all versions of the method and composition of matter disclosed herein, the armored surface may be calcined for about 30 minutes to about 24 hours, at a temperature of about 400° C. to about 1500° C. or for about 1 hour to about 12 hours, at a temperature of about 400° C. to about 1000° C. Calcining times and temperatures above and/or below these ranges are explicitly within the scope of this disclosure.

The protective thin film may be from about 1 nm thick to about 100 nm thick, or from about 1 nm thick to about 75 nm thick, or from about 1 nm thick to about 50 nm thick, or from about 1 nm thick to about 10 nm thick. Protective thin films thicker or thinner than these stated ranges are explicitly within the scope of this disclosure.

Also disclosed herein is a composition of matter produced by any of the above-described methods.

Still further disclosed herein is a composition of matter comprising a metal or metal-containing particle supported on a surface; and a protective thin film of a material of sufficient thickness to overcoat the metal or metal-containing particle and the surface, thereby yielding an armored surface; wherein the protective surface defines channels that expose a portion of the metal- or metal-containing particle to the surrounding environment.

In the same fashion as noted above with respect to the method, the composition of matter may comprise a protective thin film comprising a material selected form the group consisting of oxides, nitrides, carbides, and metals. The protective thin film may, for example, comprise a material selected from the group consisting of $AlO_x$, $HfO_x$, $HfSiO_x$, $LaO_x$, $SiO_x$, STO, $TaO_x$, $TiO_x$, $ZnO_x$, $ZrO_x$, $WO_x$, $CeO_x$, $MgO_x$, $AlN_x$, $HfN_x$, $SiN_x$, $TaN_x$, $TiN_x$, $AlC_x$, $ZrC_x$, $TiC_x$, $WC_x$, $CeC_x$, and $MgC_x$, wherein subscript "x" is a real, rational number greater than zero. The metal or metal-containing particle may comprise any metal (either alone or in combination with other metals), including base metals, noble metals, and any combination thereof. For example, the metal or metal-containing particle may comprise a metal selected from the group consisting of iron (Fe), nickel (Ni), copper (Cu), zinc (Zn), and lead (Pb).

The protective thin film overcoating the metal and the surface may be from about 1 nm thick to about 100 nm thick, or from about 1 nm thick to about 75 nm thick, or from about 1 nm thick to about 50 nm thick, or from about 1 nm thick to about 10 nm thick.

Also disclosed herein is a method of performing a heterogeneous catalytic reaction. The method comprises conducting a condensed-phase, heterogeneous catalyzed reaction in the presence of a supported catalyst, the supported catalyst comprising a metal or metal-containing particle supported on a surface; and a protective thin film of a material of sufficient thickness to overcoat the metal or metal-containing particle and the surface, thereby yielding an armored surface, wherein the protective surface defines channels that expose a portion of the metal- or metal-containing particle to the surrounding environment.

As described herein, calcining the armoring layer opens up pores and provides access to the metal or metal-containing particles underneath the overcoated layer. This allows particles to be protected from leaching and sintering, but also provides physical access to the particles so that they can exert their respective catalytic activities. Unexpectedly, the coating stabilizes the underlying metal particles against both sintering and leaching in both organic condensed-phase reaction media (e.g., liquid butanol) and in aqueous condensed-phase reaction media.

As used herein, the terms "metal" and "metal-containing" explicitly encompass any metal, catalytic or otherwise, and any entity that comprises a detectable amount of any metal, in any form (e.g., in elemental form or in the form of an oxide, nitride, carbide, etc.) Informally, the term "base metal" is typically used to refer to relatively inexpensive metals that oxidize or corrode relatively easily and react variably with diluted hydrochloric acid (HCl) to form hydrogen. Non-limiting examples of base metals include iron, nickel, copper, zinc, and lead. Copper is considered a base metal as it oxidizes relatively easily, although it does not react readily with HCl. Thus, the term "base" is used in the sense of low-born, in contrast to "noble" or "precious"

metals. Based on price alone, certain metals are often referred to as "precious metals," such as gold, silver, and platinum. The term "noble" metals is more a direct antonym to "base" metals and designates metals that are relatively resistant to corrosion and oxidation in moist air, unlike most base metals. Noble metals tend also to be precious metals due to their rarity in the earth's crust, although this is not always the case. The noble metals are generally considered to be rhenium, ruthenium, rhodium, palladium, silver, osmium, iridium, platinum, and gold. Titanium, niobium, and tantalum generally are not considered to be noble metals despite the fact that they are very resistant to corrosion.

The metal-containing catalysts described herein are typically deposited onto or impregnated into a catalyst support material. The support material may be any such support now known or developed in the future for supporting a catalyst. Explicitly included with the word "support" are refractory oxides such as alumina, zirconia, titania, hafnia, silica, etc, or mixtures of any of these. The support itself may be a metal, or a non-metal, such as carbon or silicon. The catalyst support material may be or may comprise rare earth-modified refractory metal oxides, where the rare earth may be any rare earth metal, for example, lanthanum or yttrium; and/or alkali earth metal-modified refractory oxides.

Numerical ranges as used herein are intended to include every number and subset of numbers contained within that range, whether specifically disclosed or not. Further, these numerical ranges should be construed as providing support for a claim directed to any number or subset of numbers within that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in chemistry, heterogeneous catalysis, or related fields.

BRIEF DESCRIPTION OF THE DRAWINGS

FIG. 4A depicts the spectra of 45ALD/Cu/γ$Al_2O_3$ prior to calcination (bottom trace), after calcination at 700° C. for 2 h (middle trace), and after calcination at 700° C. for 2 h (top trace). FIG. 4B depicts the spectra of 45ALD/Cu/$TiO_2$ prior to calcination (bottom trace), after calcination at 700° C. for 2 h (middle trace), and after calcination at 700° C. for 2 h (top trace). Spinning sidebands are indicated by (*).

FIG. 5A depicts the spectra of Cu/γ$Al_2O_3$ (non-coated). FIG. 5B depicts the spectra for ALD over-coated Cu/γ$Al_2O_3$. Cu foil is shown on both plots for comparison.

DETAILED DESCRIPTION

Figure 1A:
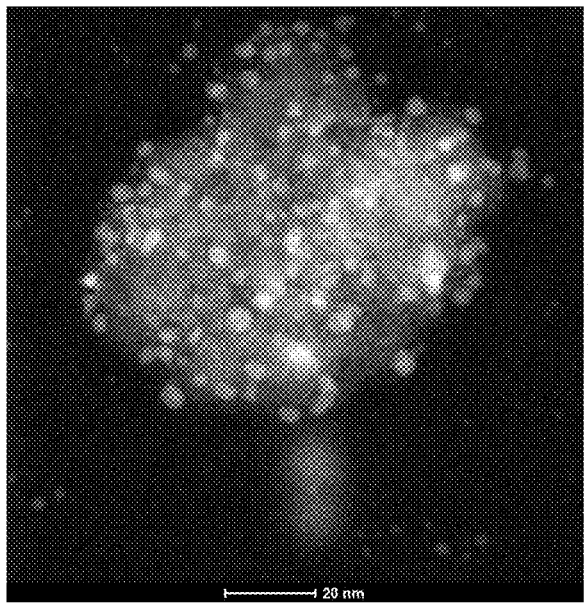
FIG. 1A is a scanning transmission electron microscopy (STEM) photograph of a base metal catalyst (copper nanoparticles) deposited on a high-surface area support (γ-alumina) via incipient wetness impregnation.

Disclosed herein is a new method to armor the particles of a metal (e.g., copper) on a high surface area support (e.g., $\gamma$-alumina) by coating the metal with a protective coating of atomic thickness—typically from about 1 to about 100 nm thick. At the heart of the method is depositing the protective coating and then calcining the coating to open up pores or channels that expose the protected metal particle so that it can (for example) function as a catalyst, yet still protect the metal particle from degradation via coking, sintering, or leaching into the reaction medium. In the working examples described herein, a metal oxide overcoat is deposited via atomic layer deposition onto a copper nanoparticle catalyst. This oxide overcoat is shown to provide resistance against sintering and leaching of the metal, without significantly affecting the kinetic behavior or structure of the underlying metal catalyst. (5, 6)

ALD is a true "nano" technology. It allows ultra-thin films of a few nanometers to be deposited in a precisely controlled way. The two defining characteristics of ALD are (1) that the process is done cyclically, with each cycle resulting in the formation of a self-limiting atomic layer of growth; (2) that the ultimate atomic thin-film created is highly conformal of the underlying substrate. (7) Equipment to implement ALD is commercially available from a number of sources. Thus, the ALD process itself will not be described in any detail here. For example, ALD equipment is available from Oxford Instruments (Oxfordshire, UK), which makes and markets the "FlexAL"®-brand and "OpAL"®brand Atomic Layer Deposition Systems. Because the ALD process deposits precisely one atomic layer in each cycle, extremely fine control over the deposition process is obtained at the nanometer scale. As noted earlier, conformal coating can be achieved using ALD even on high aspect ratio substrates and complex structures. ALD yields pinhole-free and particle-free deposition. Most notable is that a very wide variety of materials can be deposited using ALD, including (but not limited to) oxides such as $AlO_x$, $HfO_x$, $HfSiO_x$, $LaO_x$, $SiO_x$, STO, $TaO_x$, $TiO_x$, $ZnO_x$, $ZrO_x$, $WO_x$, $CeO_x$, $MgO_x$, etc.; nitrides such as $AlN_x$, $HfN_x$, $SiN_x$, $TaN_x$, and $TiN_x$, etc.; carbides such as $AlC_x$, $ZrC_x$, $TiC_x$, $WC_x$, $CeC_x$, $MgC_x$, etc., where "x" is a real, rational number greater than zero; and metals such as Cu, Pt, Ru, and W. In the presently described process, the "armoring" overcoat may be any element, compound, combination of compounds, or composition that can be deposited using atomic layer depositions. Oxide, nitrides, and carbides are the preferred coatings.

The ALD process and equipment to practice ALD is described extensively in the public literature. Further background information on a specific version of ALD is described in U.S. Pat. No. 6,287,965, issued Sep. 11, 2001, to Kang et al. See also U.S. Pat. No. 6,270,572, titled "Method For Manufacturing Thin Film Using Atomic Layer Deposition" issued Aug. 7, 2001, to Kim et al. Both of these patents are incorporated herein by reference. Further background information on ALD is available in the "Handbook Of Thin Film Materials", a five-volume set published Oct. 15, 2001, by Academic Press of San Diego, Calif., ISBN: 0125129084. Chapter 2 of Volume 1 is titled "Atomic Layer Deposition," and was authored by Mikko Ritala and Markku Leskela.

The ALD layer has a number of characteristics that make it particularly well suited for application to a metal-containing catalyst on a support. One characteristic is an ability to deposit very thin nanoscale layers, as noted earlier. Each individual layer has a thickness on the order a nanometer or less. This is very useful to build a multilayer coating that is sufficiently thick and robust to protect the metal-containing catalyst, yet sufficiently thin that calcining the overcoat will open up channels that allow chemicals to access the surface of the metal-containing catalyst. Another advantageous characteristic is that the self-limiting nature of ALD allows extremely precise control of deposition thickness. Because ALD is based on self-limiting reactions (which is not the case for chemical vapor deposition), each cycle deposits approximately a monolayer, with a thickness on the order of a nanometer or less. The layers may be built up, monolayer-by-monolayer. The resulting ALD layers are conformal, uniform in thickness, and pinhole free. The nanoscale thickness and good deposition thickness control is well suited for the minute dimensions used in, for example, nanoparticulate catalysts.

ALD also enables very conformal coatings on even complex exposed three-dimensional surfaces. This allows coating metal-containing catalysts that have gaps, cavities, pores, porous regions, trenches, out-of-sight surfaces, and high aspect ratio structures provided that a reactant gaseous species has access to the surface (i.e., is not entirely blocked). The highly conformal layers afforded by ALD are well suited for the often complex three-dimensional, high surface area structures used in heterogeneous catalysis. Because ALD deposits substantially conformal layers having uniform thickness on both line-of-sight and out-of-site surfaces, the entire catalytic surface can be protected from sintering, leaching, and coking. In short, the ability to create highly conformal, regular coatings of customizable thickness makes ALD well-suited as a coating method for catalysts having complex geometries.

Still another advantageous characteristic of ALD is reduced deposition temperatures compared to other methods such as certain types of chemical vapor deposition (CVD). Thus, ALD is generally the preferred method for forming the armoring layer. However, CVD and other thin film forming methodologies may also be used in the present method. The high temperatures typically used in conventional CVD may cause the very sintering and degradation of the catalyst that the present method is designed to prevent. For example, due to different coefficients of thermal expansion between the deposited metal-containing catalyst and the support on which the catalyst is deposited, the high processing temperature of conventional CVD may have adverse effects on integrity of the catalyst. The deposition temperature of ALD is typically significantly lower than the temperatures used in CVD. Therefore, there is reduced thermal stress on the catalyst during the coating process itself. As noted above, however, there are low temperature forms of CVD and those CVD methods can be employed in the present method if dictated by the nature of the support and metal or metal-containing catalyst being used. ALD generally allows for deposition of atomically thin films at relatively low temperatures, which do not damage the mechanical integrity of the supported catalyst. Industrial-scale reaction equipment is already available for ALD, CVD, and the other deposition methods disclosed herein.

To demonstrate the present coating process and the functionality of the resulting product, copper oxide nanoparticles deposited onto an aluminum oxide support were used as a model system. The armoring overcoats employed were deposited onto copper oxide nanoparticles synthesized by incipient wetness impregnation of γAl$_2$O$_3$ with an aqueous solution of Cu(NO$_3$)$_2$×3H$_2$O. The catalyst was then reduced in flowing H$_2$ and passivated in dilute oxygen. A STEM photograph of the copper-containing catalyst is shown in FIG. 1A. The photograph in FIG. 1A was taken before the overcoat layers were deposited by ALD with 45 alternating cycles of trimethyl alumina and water in a fluidized bed reactor at 200° C. After the ALD overcoating, the metal nanoparticles were completely encapsulated by the amorphous alumina overcoat. See FIG. 1B. The arrow in the figure points to the amorphous aluminum overcoat. After treatment at 700° C. for two hours the overcoat developed significant porosity, and the underlying copper particles were re-exposed. See FIG. 1C, which is a STEM photograph of the coated, heat-treated catalyst.

Figure 1B:
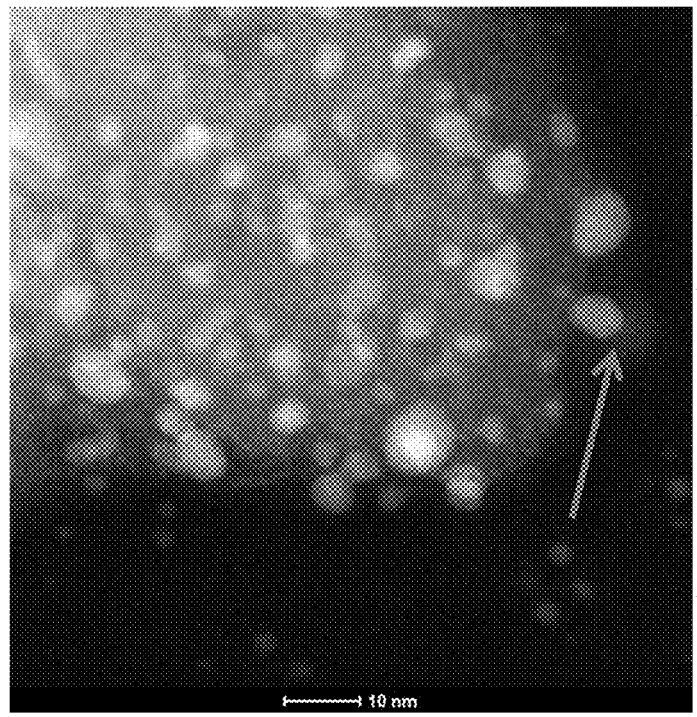
FIG. 1B is a STEM photograph of the supported catalyst depicted in FIG. 1A after 45 cycles of atomic layer deposition (ALD) of a metal oxide overcoat (in this case, $Al_2O_3$). The arrow points to the ALD coating
Figure 1C:
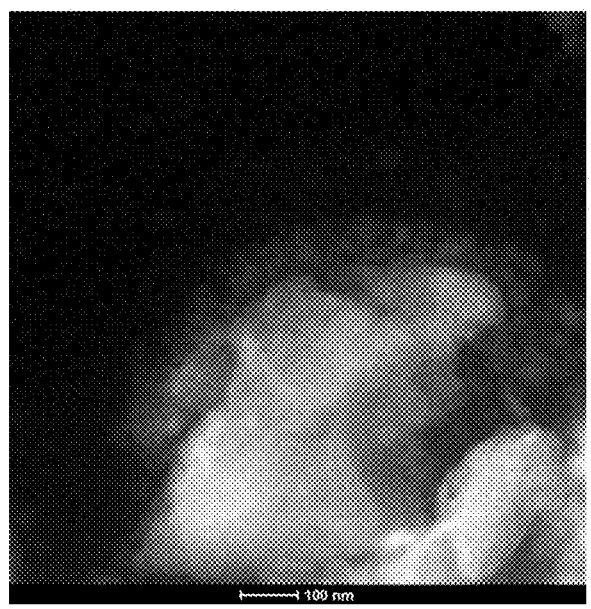
FIG. 1C is a STEM photograph of the supported and ALD over-coated catalyst depicted in FIG. 1B after heating to 700° C. for two hours.
Figure 1D:
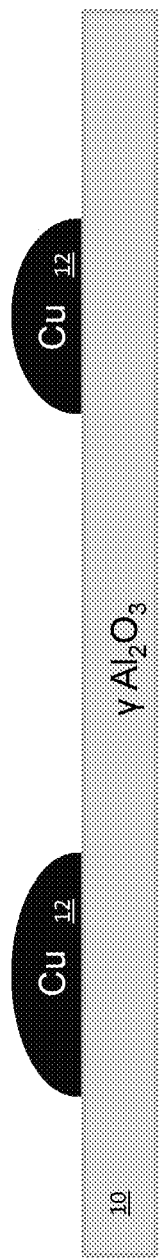
FIG. 1D is a schematic diagram of a copper catalyst deposited onto an aluminum oxide substrate in conventional fashion.
Figure 1E:
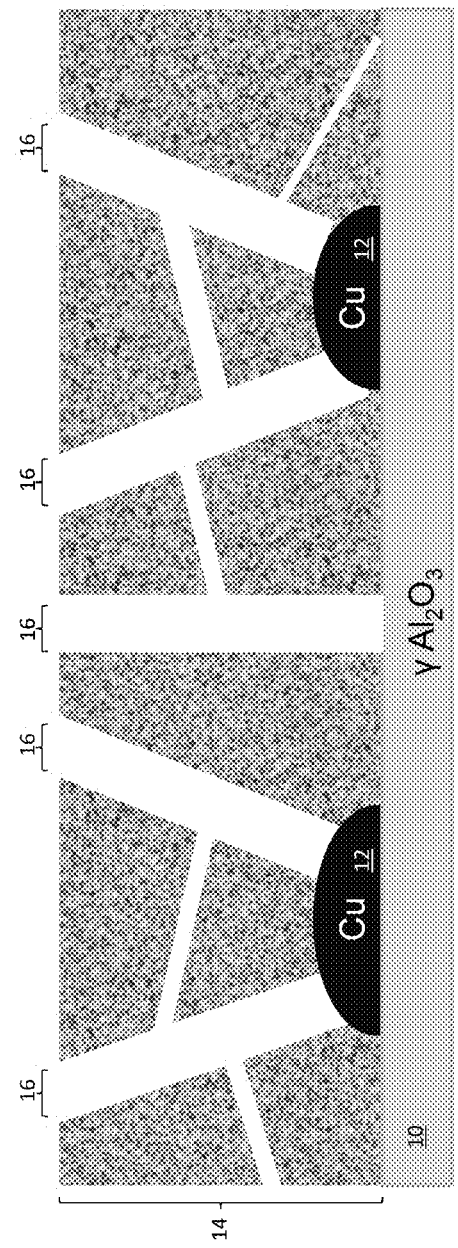
FIG. 1E is a schematic diagram of a copper catalyst deposited on a substrate and over-coated with an ALD-deposited, armoring layer, and then calcined to open pores that provide physical access to the copper particles.

Schematic representations of the photographs shown in FIGS. 1A and 1C are presented in FIGS. 1D and 1E, respectively. FIG. 1D schematically depicts the copper nanoparticles 12, deposited on the substrate 10. As shown in FIG. 1D, the copper nanoparticles are exposed to the reaction medium, and thus can (and typically do) either sinter into larger agglomerations whose surface area is greatly reduced as compared to the originally deposited nanoparticles, or leach into the reaction medium (especially when the reaction medium is aqueous). In reactions where coking is a problem, the exposed metal in FIG. 1D will be smothered with coke and be deactivated. FIG. 1E depicts the catalyst after it has been overcoated by ALD and then calcined. As shown in FIG. 1E, the copper nanoparticles 12, deposited on the substrate 10, are now overlaid with a armoring layer 14 which includes pores or channels 16 that provide physical access to the surface of the metal-containing catalyst. Although the metal-containing catalyst can be accessed by the reaction medium, the catalyst is armored against sintering, leaching, and coking.

The porosity of the oxide overcoat was characterized by Brunauer-Emmett-Teller (BET) surface area and copper surface site measurements. (Table 1) Prior to ALD treatment, the surface area of the support was 210 m$^2$ g$^{-1}$ before the copper was impregnated onto the support and 190 m$^2$ g$^{-1}$ after the copper was impregnated onto the support. After reduction in H$_2$ at 300° C. (5 hours, 0.5° C. min$^{-1}$) the Cu/γAl$_2$O$_3$ catalyst had 53 μmol g$^{-1}$ of Cu(0) sites, as titrated by a standard N$_2$O flow chemisorption method. (8) The ALD-overcoated samples exhibited a significant decrease in surface area (~16 m$^2$ g$^{-1}$) and pore volume due to the conformal nature of the ALD process filling the pores of the support and creating a continuous overcoat layer. Additionally, metallic copper surface sites were not detectable by N$_2$O titration on the overcoated catalyst after treatment in H$_2$ at 300° C. In contrast, treating the ALD-coated support at 700° C. for two hours in either air or inert gas led to an increase in the surface area and pore volume, indicating the formation of porosity in the overcoat. Importantly, the calcination step followed by reduction of the sample in H$_2$ re-exposed the copper nanoparticles and increased the number of Cu(0) surface sites measured by N$_2$O titration to 23 μmol g$^{-1}$.

TABLE 1

Copper surface site density, total surface area from BET isotherms, and pore size and volume from Barret-Joyner-Halenda (BJH) desorption.

| Material | Cu$^0$ (umol g$^{-1}$) | Surface Area (m$^2$ g$^{-1}$) | Pore Size (nm) | Pore Volume (cm$^3$ g$^{-1}$) |
|---|---|---|---|---|
| γAl$_2$O$_3$ | — | 210 | 7.1 | 0.52 |
| 45ALD/γAl$_2$O$_3$ | — | 2 | — | 0.003 |
| 45ALD/γAl$_2$O$_3$-700 | — | 63 | 3.5 | 0.11 |
| Cu/γAl$_2$O$_3$ | 53 | 190 | 7.1 | 0.45 |
| 45ALD/Cu/γAl$_2$O$_3$ | 0 | 16 | — | 0.03 |
| 45ALD/Cu/γAl$_2$O$_3$-700 | 23 | 39 | 3.4 | 0.08 |
| 45ALD/Cu/γAl$_2$O$_3$-700Inert | 21 | 59 | 3.5 | 0.10 |

Direct evidence for the formation of the overcoat and the development of porosity after calcination is apparent in the STEM images presented in FIGS. 1A, 1B, and 1C. FIG. 1A shows the copper supported on γAl$_2$O$_3$ without overcoating (Cu/γAl$_2$O$_3$), and FIG. 1B is an image after overcoating the sample with 45 ALD cycles (45ALD/Cu/γAl$_2$O$_3$), but prior to calcining. A continuous layer (about 4 nm thick) can be seen uniformly covering the nanoparticles and support. See the arrow in FIG. 1B. The overcoat appears to be homogeneous and of constant density, consistent with a lack of porosity. There is also no evidence of crystallinity within the overcoat. FIG. 1C shows the effect of calcining the overcoated sample in air at 700° C. (45ALD/Cu/γAl$_2$O$_3$-700). The overcoat has lost the homogeneity and constant density of FIG. 1B, indicative of voids and pores in the overcoat.

To test the catalytic activity of Cu/γAl$_2$O$_3$ and 45ALD/Cu/γAl$_2$O$_3$-700, this ALD-coated catalyst was used to catalyze the condensed-phase hydrogenation of furfural to furfuryl alcohol in butanol as a solvent. This reaction was chosen as a test model because it is an example of an industrially relevant copper-catalyzed hydrogenation. The estimated global production of furfuryl alcohol exceeds 250,000 tons per year. Furfuryl alcohol is used in many applications, including resins, biocides, flavorings, pharmaceuticals, and as a specialty chemical precursor, and as a solvent. (9) In addition, furfural is derived from the hemicellulose portion of biomass. Thus, the industrial importance of this hydrogenation reaction is expected to increase as industries move toward renewable feedstocks.

Figure 2:
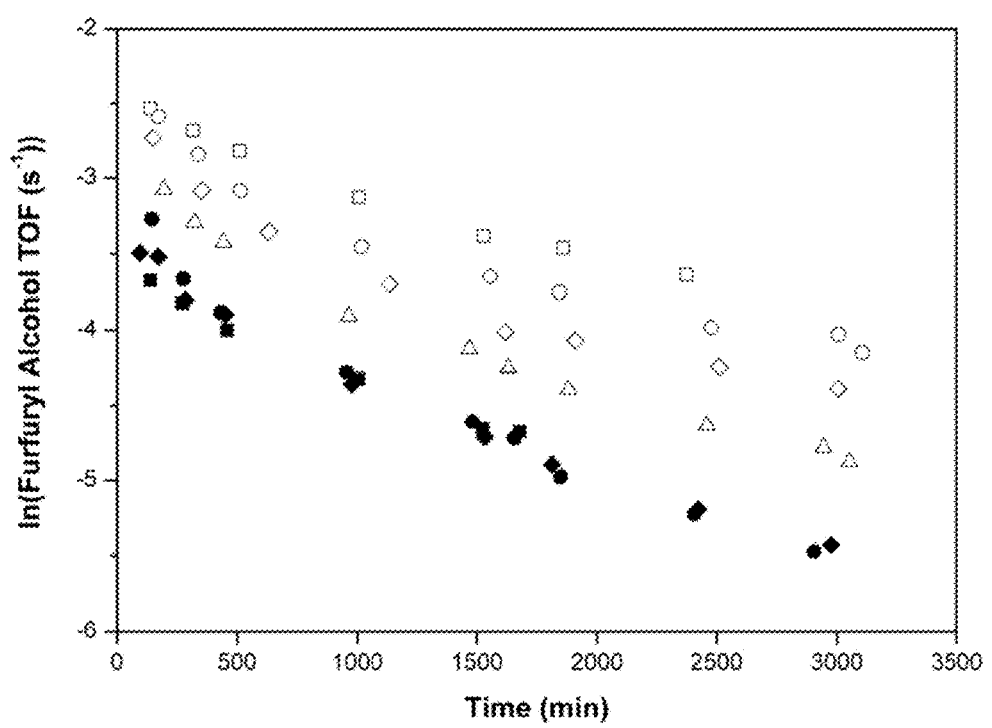
FIG. 2 is a graph depicting the first-order deactivation curves for conventional, non-coated Cu/γ-alumina (fresh □, regenerated×1 ○, regenerated×2 ◇, regenerated×3 △) and the same catalyst after 45 cycles of ALD overcoating with $Al_2O_3$ and heat-treated at 700° C. for two hours (fresh ■, regenerated×1 ●, regenerated×2 ◆). As shown in the figure, the non-coated catalysts exhibit irreversible deactivation, whereas the ALD-armored catalyst (45ALD/Cu/γ$Al_2O_3$-700° C.) exhibits full regenerability.

FIG. 2 is a graph depicting the rate of furfuryl alcohol formation over the Cu/γ-Al$_2$O$_3$ catalyst versus time on stream in a continuous flow reactor. (Key: non-coated Cu/γ-alumina: fresh □, regenerated×1 ○, regenerated×2 ◇, regenerated×3 △; the same catalyst after 45 cycles of ALD overcoating with Al$_2$O$_3$ and heat-treated at 700° C. for two hours: fresh ■, regenerated×1 ●, regenerated×2 ♦.) The linearity of this semi-log plot indicates that this catalyst deactivates with time in a first order process. Deactivation of the catalyst by the deposition of carbonaceous species (i.e., coke) on the catalyst would be reversible upon calcination in air, whereas deactivation by leaching or sintering of copper would be irreversible. It can be seen in FIG. 2 that the deactivation of Cu/γAl$_2$O$_3$ (open symbols) is not completely reversible upon calcination in air followed by reduction in H$_2$, indicating the existence of sintering and leaching. Moreover, each successive regeneration results in a further loss of activity and an increase in the first order deactivation rate constant, as can be seen from the increase in the magnitude of the slope of the deactivation curves in FIG. 2 (−4.7×10$^4$ min$^{-1}$ to −5.9×10$^4$ min$^{-1}$, open symbols).

Figure 1F:
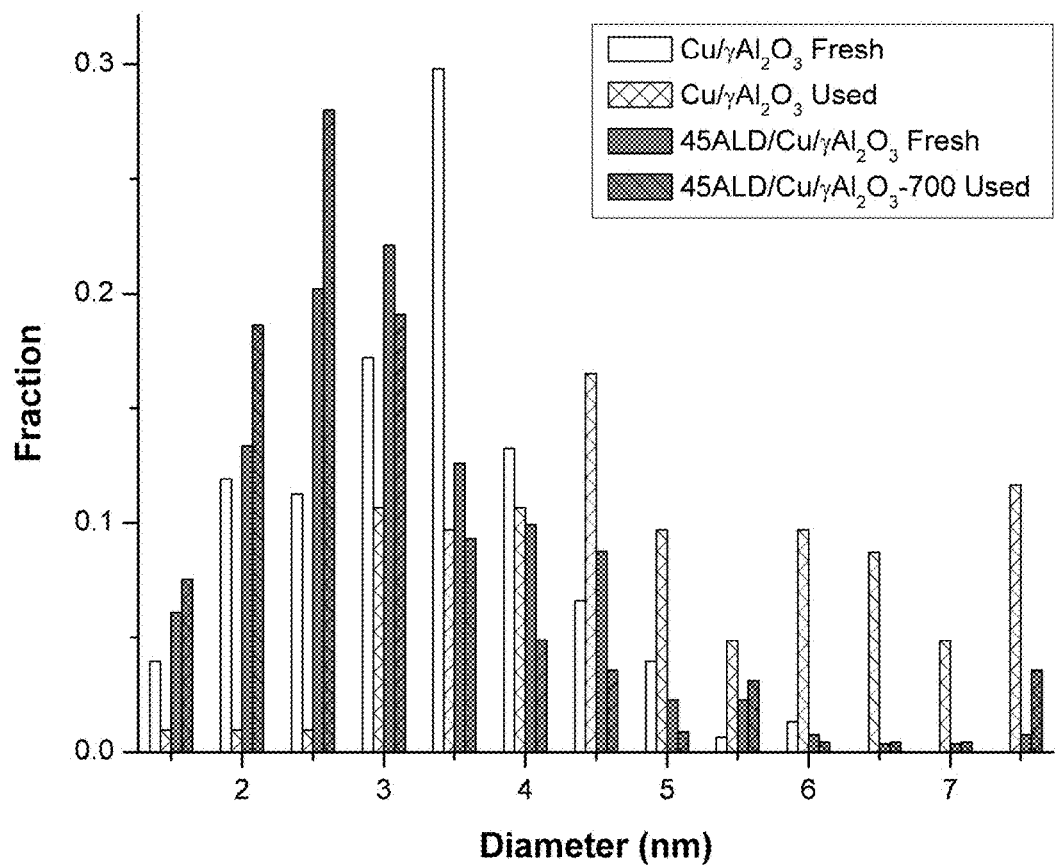
FIG. 1F is a histogram depicting the particle size distribution of the non-coated supported catalyst shown in FIG. 1A when fresh and after use, and for the ALD over-coated catalyst when fresh and after use.

The origin of the irreversible loss of catalytic activity under condensed-phase hydrogenation of furfural was investigated using STEM to determine the size distribution of the copper nanoparticles before and after reaction. As seen in the histogram shown in FIG. 1F, the average size of the copper particles was 3.0 nm before reaction, whereas the average particle size increased to 4.9 nm after 3 cycles of reaction and regeneration. Additionally, inductively coupled plasma atomic emission spectroscopy (ICP-AES) was used to analyze the metal loading of the catalyst before and after reaction. The Cu/γAl$_2$O$_3$ had metal loading by ICP-AES of 5.9%, before reaction, whereas the metal loading had decreased to 5.0% after 3 cycles of reaction and regeneration, indicating leaching of copper from the catalyst.

The performance of the 45ALD/Cu/γAl$_2$O$_3$-700 catalyst was remarkably different from the Cu/γAl$_2$O$_3$ catalyst for the same reaction and regeneration conditions. While the ALD-overcoated catalyst still deactivated during time on stream, the initial activity was fully recovered after calcination and re-reduction. (FIG. 2, filled symbols). This behavior indicates that while the catalyst in this reaction still suffers from coking, the irreversible sintering and leaching of the particles was prevented by the overcoating. The analysis of the copper particle size before and after reaction (FIG. 1F) further confirms that the ALD overcoat prevented sintering of the copper nanoparticles. The initial copper particle size for 45ALD/Cu/γAl$_2$O$_3$ before the calcination to form porosity in the overcoat was 2.9 nm, essentially identical to that of the Cu/γAl$_2$O$_3$ catalyst. After calcination at 700° C., followed by three cycles of reaction and regeneration, the average particle size and the particle size distribution were essentially unchanged (2.8 nm, FIG. 1F). In addition, the copper loading of the catalyst as measured by ICP-AES was 2.4% before reaction and 2.5% after 3 cycles reaction and regeneration, indicating that the ALD-overcoat eliminated leaching of copper during condensed-phase hydrogenation of furfural.

Figure 3:
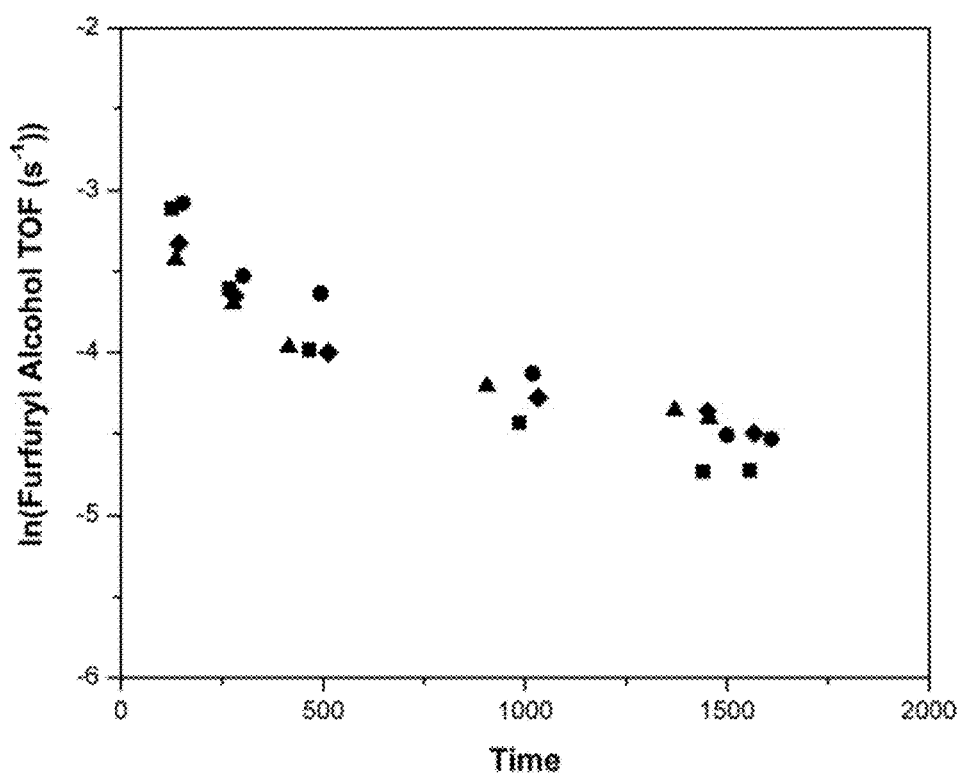
FIG. 3 is a graph depicting the results of a stability study for the (45ALD/γCu/$Al_2O_3$-700° C. catalyst using water as the reaction solvent (fresh ■, regenerated×1 ●, regenerated×2 ◆, regenerated×3 ▲). The ability to regain all of the initial activity indicates that the only deactivation occurring in this study is reversible coking of the catalyst (rather than sintering or leaching of the catalyst).

The results illustrated by FIG. 2 demonstrate the remarkable stabilization of metallic nanoparticles by the ALD overcoat during hydrogenation of furfural in liquid butanol solvent. As a further test of the stability imparted by the ALD overcoat, the 45ALD/Cu/γAl$_2$O$_3$-700 catalyst was used for the hydrogenation of furfural to furfuryl alcohol in liquid water at 130° C. FIG. 3 shows that even in the presence of high temperature liquid water, the ALD overcoat effectively armors the copper against sintering and leaching through a total of four (4) cycles of reaction and regeneration, without loss in initial activity or an increase in the rate of deactivation. (Key: fresh ■, regenerated×1 ●, regenerated×2 ♦, regenerated×3 ▲) These four cycles are the equivalent of a time on stream greater than 100 hours.

Figures 4A, 4B:
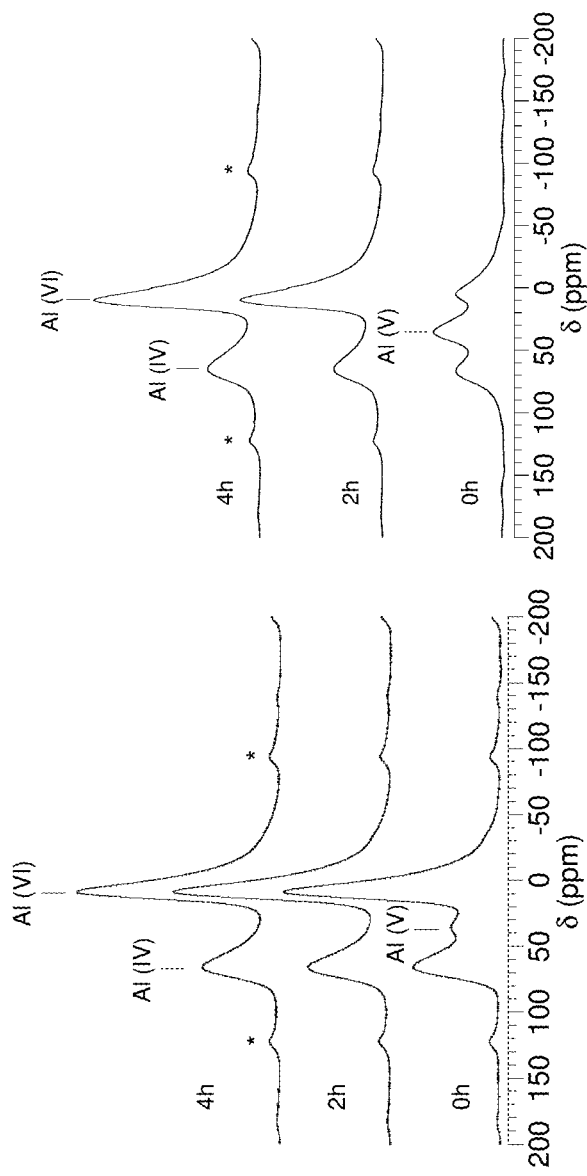
FIGS. 4A and 4B are solid-state $^{27}Al$ magic angle spinning nuclear magnetic resonance (MAS NMR) spectra.
Figure 11:
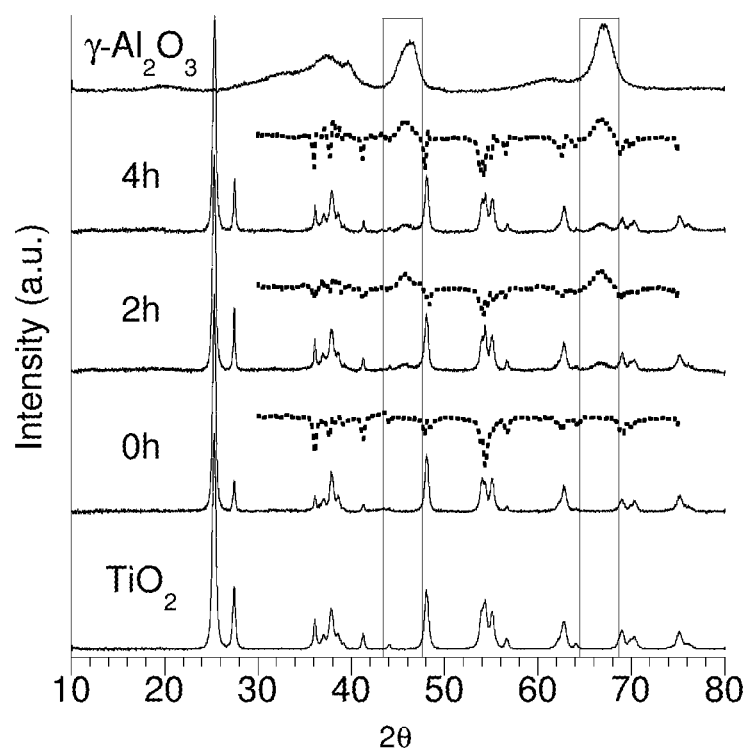
FIG. 11 depicts X-ray diffraction patterns of unmodified $\gamma$-$Al_2O_3$ (top), $TiO_2$ (bottom) and $Al_2O_3$/Cu/$TiO_2$ prior to calcination (0 h) and after calcination (2 h and 4 h). Enhanced difference patterns between $TiO_2$ and $Al_2O_3$/Cu/$TiO_2$ (2.5×) are presented as dotted lines.

The prevention of sintering and leaching would not be practically useful if the armoring overcoat blocked catalytic metal sites and prevented the reaction. As can be seen from the increase in total surface area and exposed copper surface sites in Table 1, the ALD overcoating layer undergoes a transformation when heated. The pore opening mechanism has not been explained in the literature. Thus, to gain some insight on the nature of the pores formed by heating, solid state Al$^{27}$ MAS NMR was used to probe the nature of the overcoat alumina before and after calcination. FIG. 4A depicts the spectra of 45ALD/Cu/γAl$_2$O$_3$ prior to calcination (bottom trace), after calcination at 700° C. for 2 h (middle trace), and after calcination at 700° C. for 2 h (top trace). FIG. 4B depicts the spectra of 45ALD/Cu/TiO$_2$ prior to calcination (bottom trace), after calcination at 700° C. for 2 h (middle trace), and after calcination at 700° C. for 2 h (top trace). Spinning sidebands are indicated by (*). FIGS. 4A and 4B show resonances at 9.3, 33.3, and 65.5 ppm that indicate the presence of 6-, 5-, and 4-coordinate alumina, respectively, in the overcoat layer. The presence of the 5-coordinate alumina confirms the amorphous nature of the overcoat before calcination. (10) After calcination at 700° C. the resonance at 33.3 ppm which corresponds to the 5-coordinate alumina disappears. This is observed most dramatically in FIG. 4A where the overcoat is supported on Cu/TiO$_2$ rather than on γAl$_2$O$_3$ so that the overlapping contribution from the support is eliminated. Additionally, as demonstrated by x-ray diffraction, the overcoat begins to crystallize. (See FIG. 11.) The formation of γAl$_2$O$_3$, which correlates with the conversion of the 5-coordinate alumina to higher density coordination (Table 2, below), creates voids in the overcoat as it densifies and re-exposes the underlying copper. (11)

|  | Coordination | | |
|---|---|---|---|
| Sample | Al(IV) | Al(V) | Al(VI) |
| 45ALD/Cu/Al$_2$O$_3$ | 26% | 18% | 56% |
| 45ALD/Cu/Al$_2$O$_3$-700 2 hours | 36% | — | 65% |
| 45ALD/Cu/Al$_2$O$_3$-700 4 hours | 34% | — | 66% |
| 45ALD/Cu/TiO$_2$ | 26% | 42% | 33% |
| 45ALD/Cu/TiO$_2$-700 2 hours | 28% | — | 72% |
| 45ALD/Cu/TiO$_2$-700 4 hours | 27% | — | 76% |

The remarkable stability imparted by the overcoat is likely due to a selective armoring interaction with the most weakly held metal atoms on the surface of the nanoparticle. In particular, sintering and leaching are believed to originate from under-coordinated metal surface atoms located at edges, corners, and defects. (12) Accordingly, while not being bound to any specific mechanism or underlying phenomenon, the stability imparted to the metal nanoparticles by ALD overcoating may be derived from a selective interaction of the alumina overcoat with under-coordinated metal atoms on the surface of the nanoparticles. (13, 14)

Figure 5A:
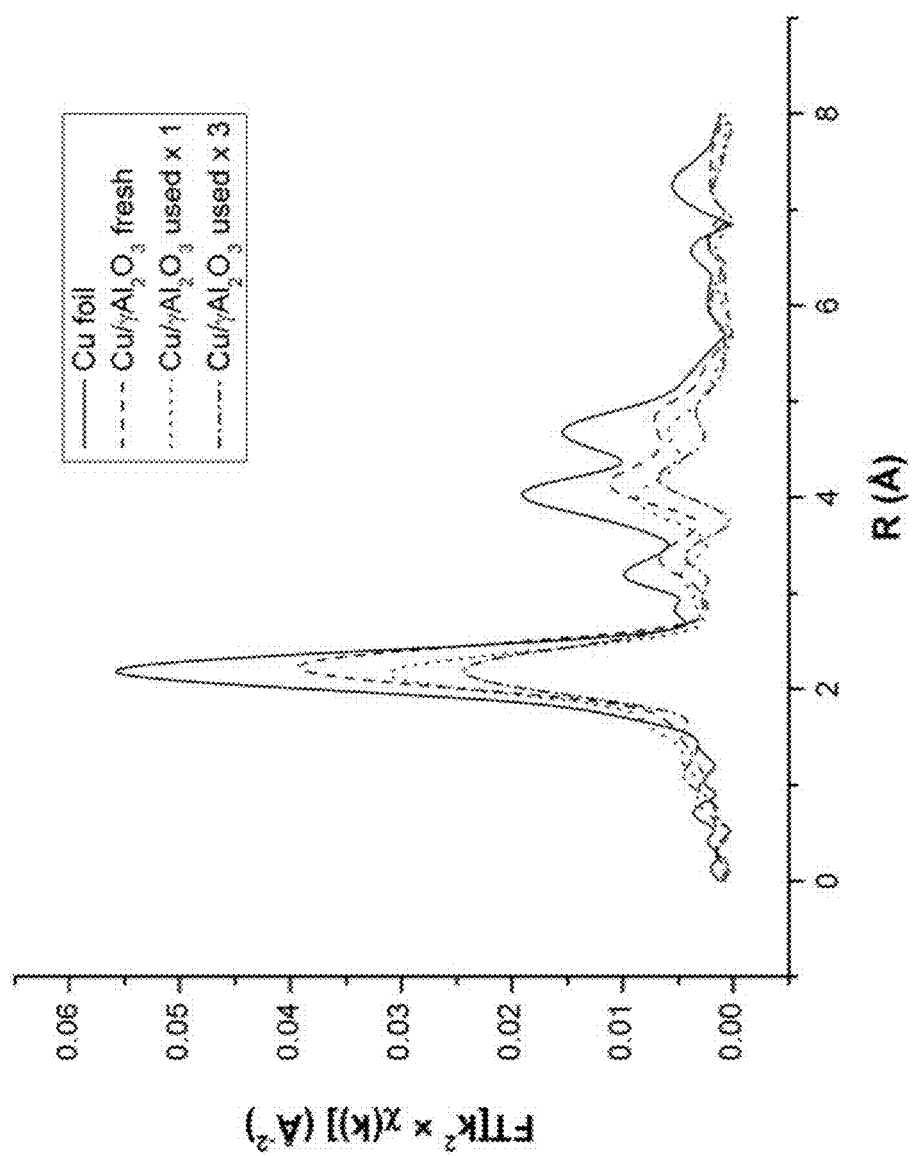
FIGS. 5A and 5B are X-ray absorption spectra of conventional (non-coated) and ALD-overcoated catalysts after different stages of synthesis and use.
Figure 5B:
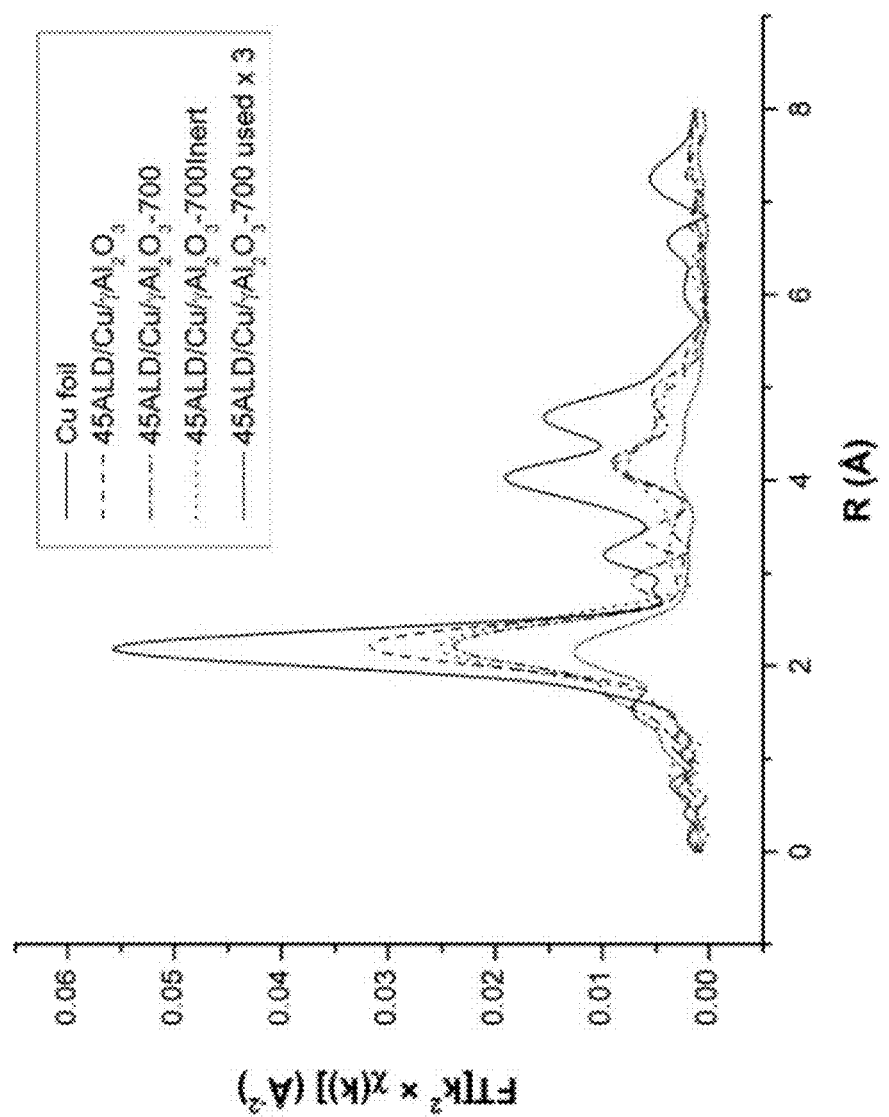

To illuminate the importance of this interaction, the possible interaction of the alumina overcoat with the copper nanoparticle was studied using x-ray adsorption spectroscopy (XAS) measurements. See FIGS. 5A and 5B. FIG. 5A depicts the spectra of Cu/γAl$_2$O$_3$ (non-coated). FIG. 5B depicts the spectra for ALD over-coated Cu/γAl$_2$O$_3$. Cu foil is shown on both plots for comparison. As seen in the R-space spectra presented in FIG. 5A, the copper atoms in the Cu/γAl$_2$O$_3$ catalyst are not coordinated to oxygen and are thus fully reduced after pretreatment in H$_2$ at 300° C. The same behavior can be seen in FIG. 5B for the 45ALD/Cu/γAl$_2$O$_3$ material. This result for the overcoated material before calcination indicates that the overcoating is sufficiently porous for H$_2$ diffusion, because H$_2$ is able to reduce the copper to the metallic state, but larger molecules like N$_2$ and N$_2$O cannot penetrate through the overcoat (thus leading to low BET surface area as measured by N$_2$ and low titration of metallic copper by N$_2$O, as seen in Table 1). The results depicted in FIG. 5B show that calcination at 700° C. leads to the formation of oxidized copper that is not reduced by treatment in H$_2$ at 300° C., as indicated by the increased signal around R=1.4 Å. The presence of this stable copper-oxygen bond after heating to 700° C. and re-reducing in H$_2$ indicates that the treatment at high temperatures leads to the armoring interaction between the aluminum overcoat and the copper nanoparticle. Moreover, this stable copper-oxygen bond even forms during treatment at high temperature in an inert atmosphere (45ALD/Cu/γAl$_2$O$_3$-700Inert), when the only oxygen present is in the overcoat itself.

Figure 7:
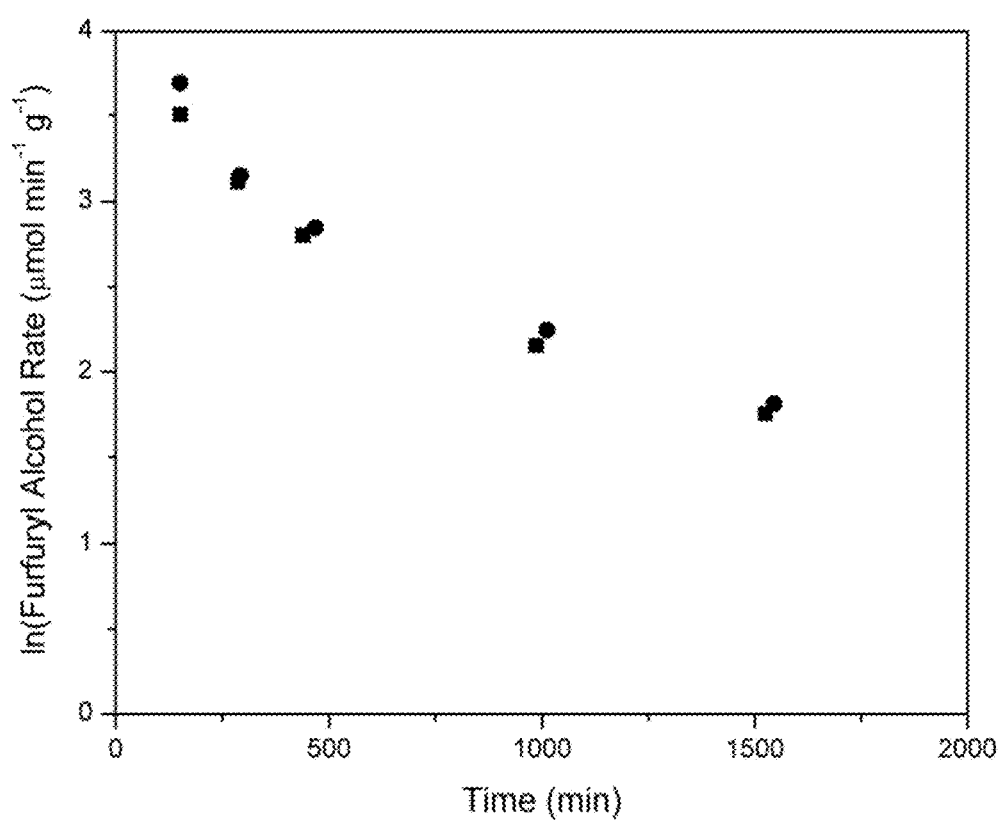
FIG. 7 is a graph depicting the results of a stability study for the (45ALD/γCu/$Al_2O_3$-700Inert catalyst (fresh ■, regenerated×1 ●). The catalyst demonstrates full regenerability.

Note that the 45ALD/Cu/γAl$_2$O$_3$-700Inert catalyst behaves in the same fashion as the (45ALD/Cu/γAl$_2$O$_3$-700 catalyst. See FIG. 7, which is a graph depicting the results of a stability study for the 45ALD/γCu/Al$_2$O$_3$-700Inert catalyst (fresh ■, regenerated×1 ●). The catalyst demonstrates full regenerability. The ability of the coated catalyst to regain all of the initial activity indicates that the only deactivation observed is reversible coking.

FIGS. 5A and 5B also compare the R-space spectra of the Cu/γAl$_2$O$_3$ and 45ALD/Cu/γAl$_2$O$_3$-700 catalysts before and after reaction. The two catalysts appear similar prior to use for condensed-phase hydrogenation of furfural. After reaction, the used 45ALD/Cu/γAl$_2$O$_3$-700 catalyst (FIG. 5B) appears to be unchanged compared to its original state (FIG. 5B), whereas the copper nanoparticles for the Cu/γAl$_2$O$_3$ catalyst (FIG. 5A) appear to decrease in size (FIG. 5A). This apparent decrease in copper particle size is not consistent with the results of STEM measurements that indicate an increase in the copper particle size after reaction; therefore, the apparent decrease in copper particle size observed by XAS is most likely caused by leaching of copper from the copper nanoparticles and re-deposition of copper onto the support, creating isolated atomic copper and/or small copper clusters. The bulk XAS technique would observe this copper as very low coordination, whereas this atomic copper would not be visible in the particle size images. In contrast to this behavior of the Cu/γAl$_2$O$_3$ catalyst, the average size determined from Cu coordination by XAS of the copper particles on the 45ALD/Cu/γAl$_2$O$_3$-700 catalyst remains the same before and after reaction kinetics studies, further demonstrating the stability imparted by the armoring overcoat. Further details of the XAS fits are provided in Table 3.

Table 3 shows further details of the results from x-ray adsorption spectroscopy experiments.

Figure 6:
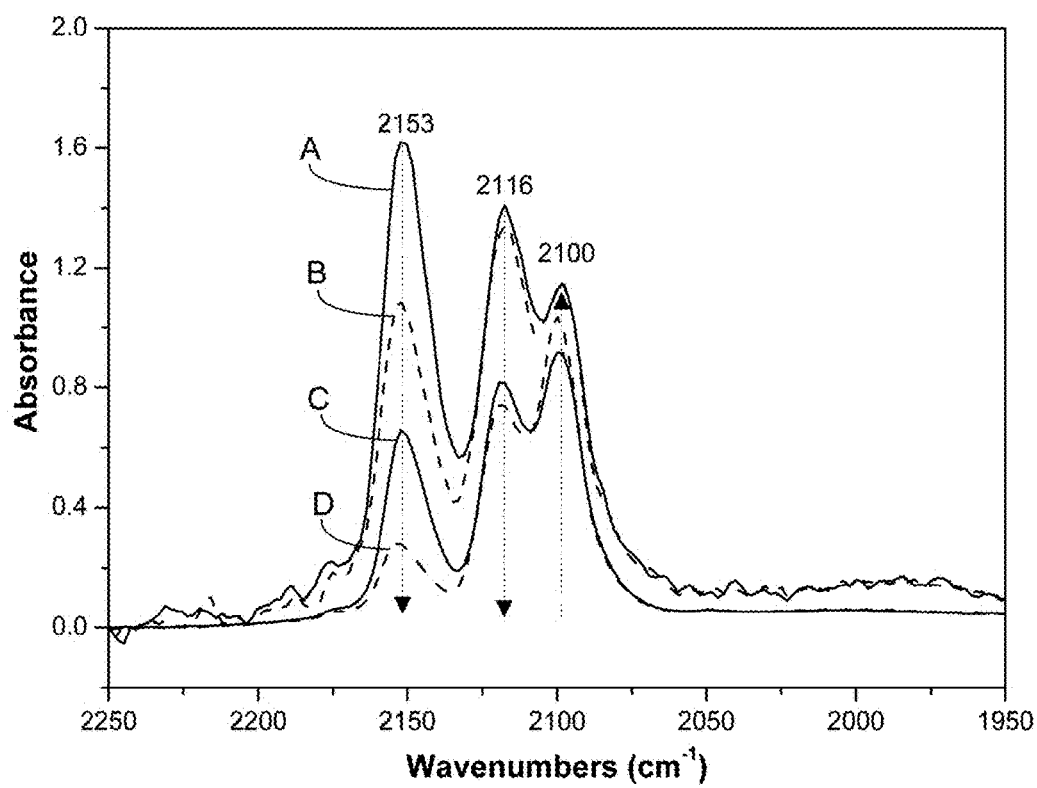
FIG. 6 depicts infrared (IR) spectra for CO on Cu/γ$Al_2O_3$ (traces C and D) and 45ALD/Cu/γ$Al_2O_3$-700 (traces A and B) at −160° C. after 17 minutes desorption time (solid) and 50 minutes desorption time (dashed). The absorbances have been normalized by the number of copper sites titrated by $N_2O$.
Figure 8A:
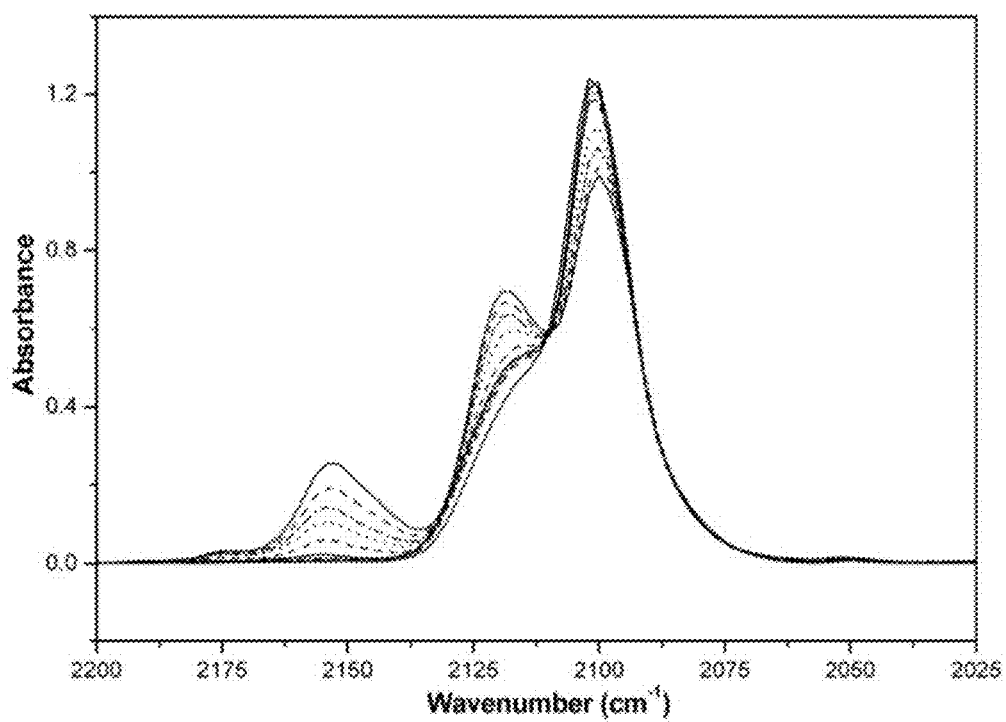
FIG. 8A is a series of IR spectra of CO desorbing from Cu/γ$Al_2O_3$ at temperatures from −155° C. to −50° C.
Figure 8B:
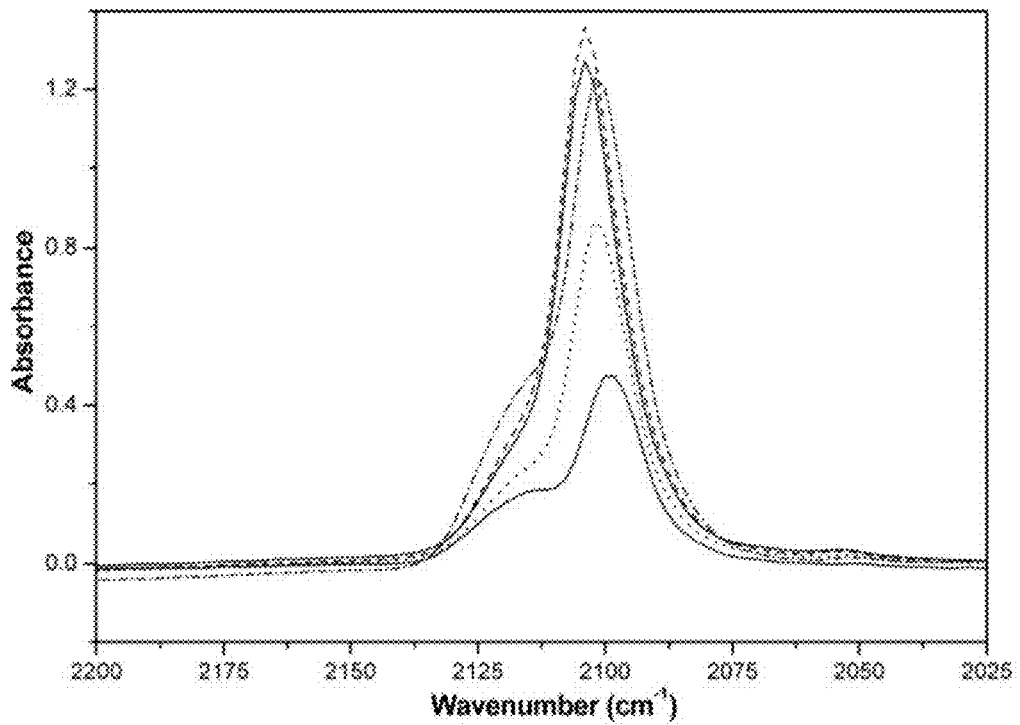
FIG. 8B is a series of IR spectra of CO desorbing from Cu/γ$Al_2O_3$ at temperatures from −50° C. to 25° C.
Figure 8C:
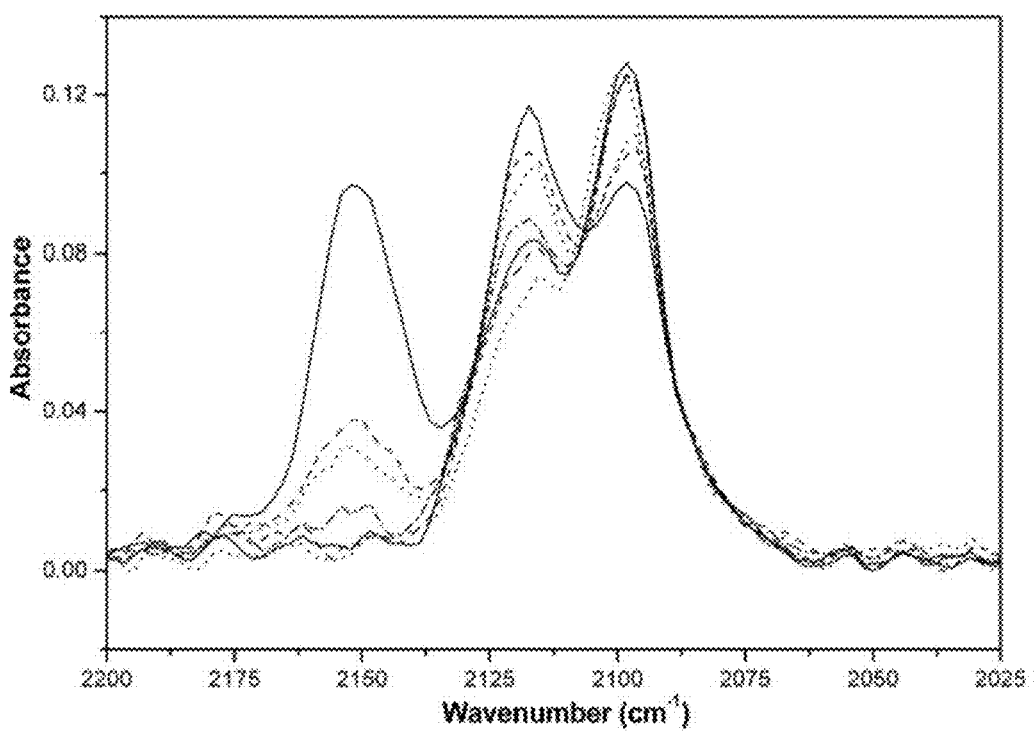
FIG. 8C is a series of IR spectra of CO desorbing from 45ALD/Cu/γ$Al_2O_3$ at temperatures from −160° C. to −50° C.
Figure 8D:
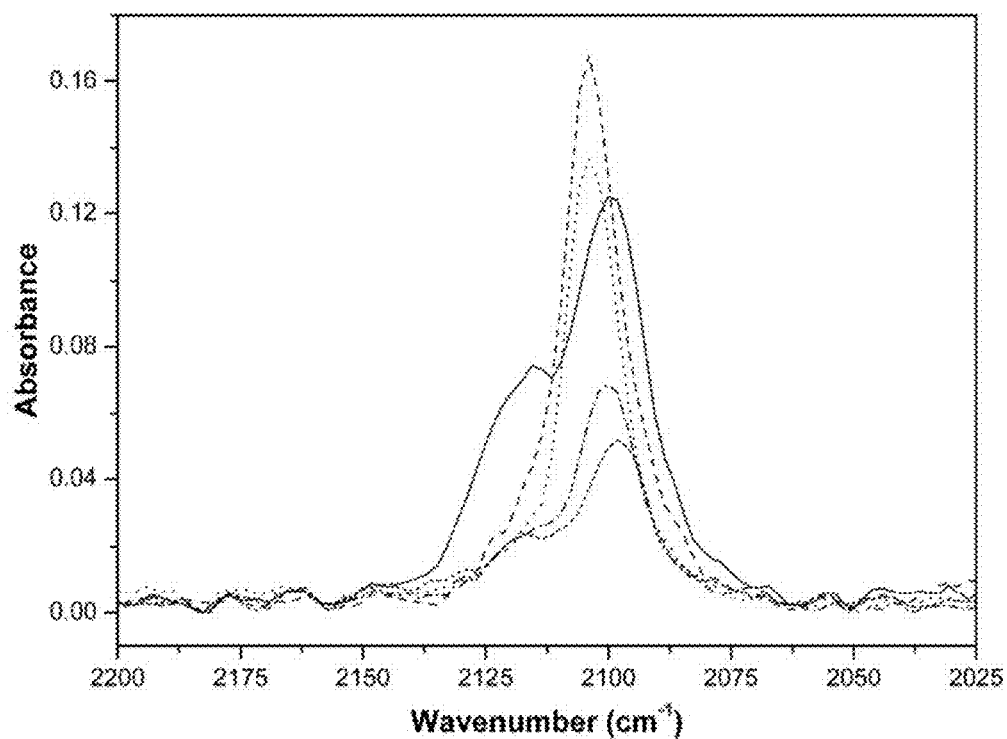
FIG. 8D is a series of IR spectra of CO desorbing from 45ALD/Cu/γ$Al_2O_3$ at temperatures from −50° C. to 25° C.

The exposed sites of the nanoparticles were further probed using infrared (IR) spectroscopic measurements of CO adsorbed on the copper surface at sub-ambient temperatures. See FIG. 6. FIG. 6 depicts infrared (IR) spectra for CO on Cu/γAl$_2$O$_3$ (traces C and D) and 45ALD/Cu/γAl$_2$O$_3$-700 (traces A and B) at $-160°$ C. after 17 minutes desorption time (solid) and 50 minutes desorption time (dashed). The absorbances have been normalized by the number of copper sites titrated by N$_2$O. See also FIGS. 8A-8D. The IR spectra for the Cu/γAl$_2$O$_3$ and 45ALD/Cu/γAl$_2$O$_3$-700 catalysts both have bands at 2100, 2116, and 2153 cm$^{-1}$. (FIG. 6) Vibrational trends calculated from density functional theory (DFT) calculations suggest that these bands correspond to CO adsorbed on or near copper atoms that are associated with oxygen species (e.g., AlO$_x$ species) bound to copper. The bands at 2116 and 2100 cm$^{-1}$ appear to be symmetric and antisymmetric stretches of CO adsorbed on adjacent under-coordinated copper sites associated with oxygen (e.g., under-coordinated copper atoms at steps) rather than dicarbonyls on a single Cu atom. (See Table 4) In agreement with this assignment, Goodman et al. assigned bands at 2091 and 2116 cm$^{-1}$ to CO adsorbed on a Cu (100) surface decorated with oxygen. (15) Upon desorption of CO, a decrease in band intensity at 2116 cm$^{-1}$ is observed coinciding with an increase in the band intensity at 2100 cm$^{-1}$, in accordance with the observations of Goodman. See FIGS. 6, 8A, and 8C. The results from the DFT calculations support the conclusion that the coupled bands at 2116 and 2100 cm$^{-1}$ are replaced by a single intermediate band at a frequency near 2104 cm$^{-1}$ as the coverage of CO on the surface decreases. See FIGS. 8B and 8D. Whereas the CO molecules adsorbed on adjacent copper sites at high CO coverage are tilted with respect to the surface normal, the CO molecules present at lower coverage are oriented perpendicular to the surface, which explains an observed increase in absorbance at lower coverage. (FIGS. 8B and 8D) These results observed in the IR spectra upon desorption of CO from the surface at progressively higher temperatures are consistent with the trends from DFT results as well. Consequently, the bands at 2100 and 2116 cm$^{-1}$ are likely due to vibrations of CO on under-coordinated copper sites associated with oxygen species.

| Sample | Condition | Scatterer | EXAFS | | | | XANES | | | True N |
| | | | N | R | $\sigma^2 \times 10^3$ | Eo | Cu(0) | Cu(I) | Cu(II) | |
|---|---|---|---|---|---|---|---|---|---|---|
| Cu/gAl$_2$O$_3$ | in air | Cu | 1.7 | 2.6 | 2 | 7.5 | 0 | 0 | 1 | — |
| | | O | 3.3 | 1.92 | 4 | -7.5 | | | | |
| Cu/gAl$_2$O$_3$ | reduced then scanned in He | CO | 9.6 | 2.53 | 1 | 7.5 | 1 | 0 | 0 | 9.6 |
| | | O | 0 | — | — | — | | | | |
| Cu/gAl$_2$O$_3$ used × 1 | reduced then scanned in He | Cu | 7.6 | 2.56 | 1 | -6.3 | 0.8 | 0 | 0.2 | 9.5 |
| | | O | 1 | 1.93 | 4 | -6.9 | | | | |
| Cu/gAl$_2$O$_3$ used × 3 | reduced then scanned in He | Cu | 6.8 | 2.52 | 2 | 6.3 | 1 | 0 | 0 | 6.8 |
| | | O | 0 | — | — | — | | | | |
| 45ALD/Cu/gAl$_2$O$_3$ | in air | Cu | 1.7 | 2.6 | 2 | -7.5 | 0 | 0 | 1 | — |
| | | O | 2.8 | 1.96 | 4 | 6.8 | | | | |
| 45ALD/Cu/gAl$_2$O$_3$ | reduced then scanned in He | Cu | 8 | 2.52 | 1 | 6.2 | 1 | 0 | 0 | 8 |
| | | O | 0 | — | — | — | | | | |
| 45ALD/Cu/gAl$_2$O$_3$ 700 | in air | Cu | 0 | — | — | — | 0 | 0 | 1 | — |
| | | O | 3.2 | 1.93 | 4 | -7.5 | | | | |
| 45ALD/Cu/gAl$_2$O$_3$ 700 | reduced then scanned in He | Cu | 3.6 | 2.54 | 2 | 7 | 0.7 | 0 | 0 | 5.1 |
| | | O | 1.9 | 1.89 | 4 | -7 | | | | |
| 45ALD/Cu/gAl$_2$O$_3$ 700 used × 3 | reduced then scanned in He | Cu | 6.7 | 2.53 | 2 | 7 | 0.8 | 0 | 0 | 8.4 |
| | | O | 1.7 | 1.97 | 4 | -0.6 | | | | |

TABLE 4

Vibrational frequencies predicted by density functional theory for CO adsorbed on a Cu(211) surface with and without oxygen. DFT is able to qualitatively predict the higher wave number adsorptions observed in the experiments.

| 3 × 3 × 3 unit cell CO Coverage | Without O | | | With 1/9 ML O | | | |
|---|---|---|---|---|---|---|---|
| | CO site | CO Diff BE (eV) | CO vib freq ($cm^{-1}$) | CO Site | O Site | CO Diff BE (eV) | CO vib freq ($cm^{-1}$) |
| 1/9 ML | Top | −0.96 | 2107 | Top | H1 | −0.97 | 2136 |
| 2/9 ML | Top, Top | −0.95 | 2124 ($v_S$), 2072 ($v_{AS}$) | Top, Top | F2 | −0.81 | 2148 ($v_S$), 2104 ($v_{AS}$) |

Under conditions of high coverage (i.e., in the presence of gaseous CO), the band at 2153 $cm^{-1}$ can be assigned to a CO physisorbed on the alumina support or overcoat. However, after long desorption times, this physisorbed CO is removed from the sample, as evidenced by control experiments conducted on alumina samples that do not contain copper. Therefore, presence of the band at 2153 $cm^{-1}$ on samples containing copper after prolonged time in flowing helium at low temperatures can be assigned to CO bound to partially oxidized copper site, e.g., a copper atom that is directly bound to oxygen atom. Similarly, Hadjiivanov observed a band at 2155 for a $CuO_x/TiO_2$ catalyst and proposed that this band is the symmetric stretching component of CO adsorbed to $Cu^+$. (16) The antisymmetric component of that stretch was assigned to a vibration located at 2110 $cm^{-1}$ and would be obscured by the stretches observed here at 2100 and 2116 $cm^{-1}$. On the $Cu/\gamma Al_2O_3$ catalyst, the oxidized $AlO_x$ sites would be located at or near the copper-support interface. On 45ALD/Cu/$\gamma Al_2O_3$-700 catalyst, these sites would be formed either at the copper-support interface or near the alumina overcoat on the copper nanoparticle. The ALD overcoating increases the number of under-coordinated copper atoms associated with $AlO_x$, as evidenced by the increase in the intensity of the bands at higher wavenumber. It is these newly covered copper sites that were previously responsible for sintering and leaching, but are now stabilized due to their interaction with the armoring alumina overcoat.

Figure 9:
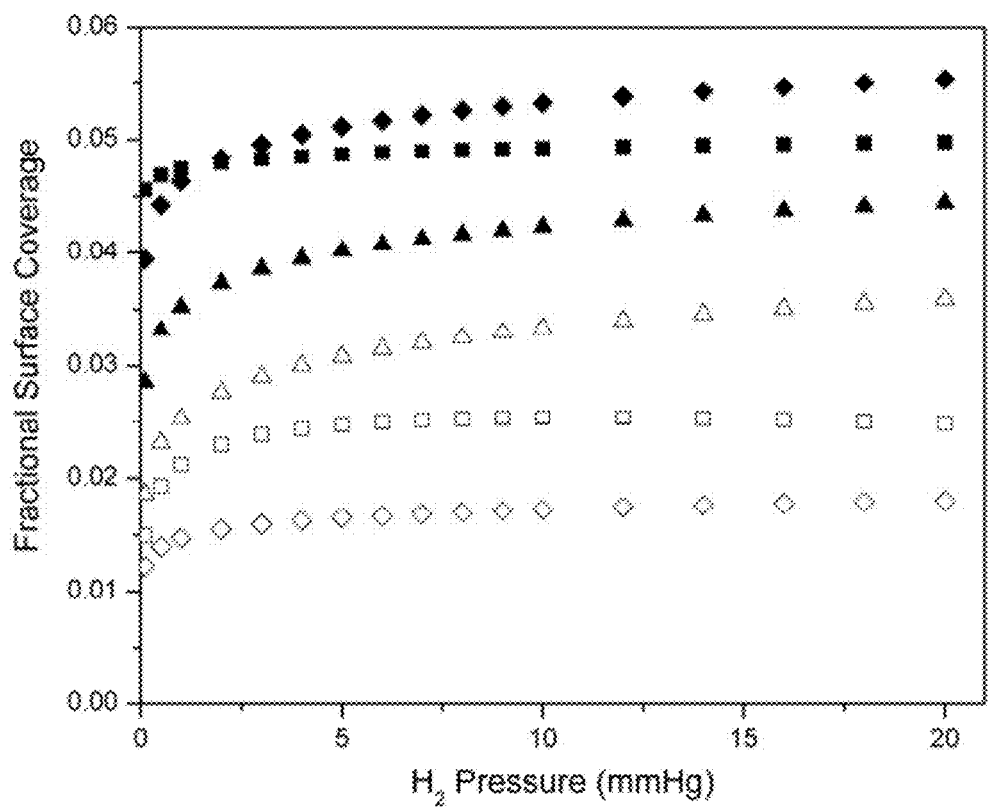
FIG. 9 is a graph depicting irreversible $H_2$ chemisorption isotherms calculated as the difference between the first and repeat isotherms. The standard, non-coated Cu/γ$Al_2O_3$ catalyst (open symbols) shows thermodynamically controlled adsorption. In contrast, the ALD-over-coated 45ALD/Cu/γ$Al_2O_3$-700 (closed symbols) demonstrates kinetically controlled adsorption.
Figure 10:
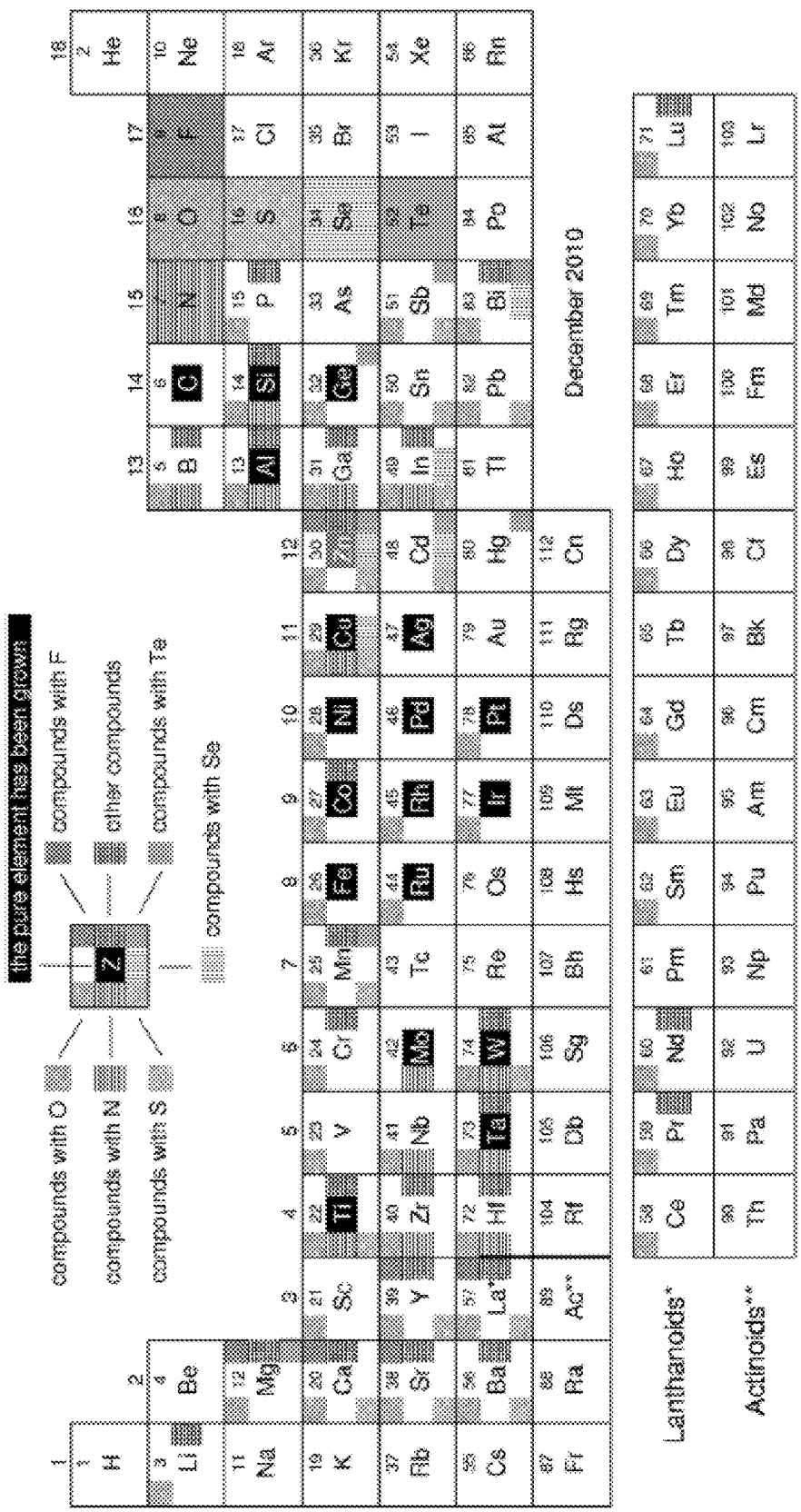
FIG. 10 is a periodic table of the elements that provides an overview of materials grown by ALD. Growth of pure elements, as well as compounds with oxygen, nitrogen, sulfur, selenenium, tellurium, fluorine, and other compounds are indicated through shadings of different types at different positions on the table.

The difference in the nature of the surface copper sites on $Cu/\gamma Al_2O_3$ and 45ALD/Cu/$\gamma Al_2O_3$-700 catalysts was also probed by measuring the irreversible adsorption of $H_2$ on these samples at various temperatures. (See FIG. 9) The dissociative adsorption of $H_2$ on copper is an activated process, with a lower barrier for copper sites with low coordination (e.g., at steps and defects). (17) The hydrogen atoms produced in this manner on the surface can subsequently diffuse to terrace sites on the surface. The $Cu/\gamma Al_2O_3$ catalyst has enough copper sites with low coordination that the dissociative adsorption of $H_2$ is sufficiently rapid to achieve high uptakes of $H_2$ at low temperatures (e.g., 30° C.). In particular, the uptake of $H_2$ decreases as the temperature of adsorption is increased, in agreement with the exothermic nature of this adsorption process. In contrast, the uptake of $H_2$ on the 45ALD/Cu/$\gamma Al_2O_3$-700 does not decrease as the adsorption temperature is increased from 30° C. to 200° C., because this ALD-overcoated catalyst does not have a sufficient number of low-coordinated copper sites to facilitate dissociation of $H_2$ at low temperatures. Additionally, the presence of $AlO_x$ species decorating the surface of the catalyst may inhibit the diffusion of H atoms on the surface away from the active sites for dissociative adsorption. Again, the conclusion is that these low-coordinated copper sites have undergone reaction with $AlO_x$ species from the ALD overcoat.

On the basis of these results, it can be concluded that the armoring ALD-overcoat acts to stabilize the base metal nanoparticles against both irreversible sintering and leaching. The high temperature calcination opens the overcoating, re-exposing the metal underneath, while maintaining a stabilizing interaction with the low coordination copper atoms on the surface of the nanoparticle that are most prone to sintering and leaching. The use of this new base metal armoring technique should be particularly useful in supplementing precious and noble metal catalysts with base metals for a wide range of traditional and new bio-renewable applications where catalyst stability is a significant challenge.

REFERENCES CITED

The following documents are incorporated herein by reference.
1. Catalysis without Precious Metals. (Wiley-VCH Verlag GmbH & Co. KGaA, 2010).
2. M. V. Twigg, M. S. Spencer, Deactivation of supported copper metal catalysts for hydrogenation reactions. Applied Catalysis A: General 212, 161 (Apr. 30, 2001).
3. M. Twigg, M. Spencer, Deactivation of Copper Metal Catalysts for Methanol Decomposition, Methanol Steam Reforming and Methanol Synthesis. Topics in Catalysis 22, 191 (2003 Apr. 1, 2003).
4. M. Besson, P. Gallezot, Deactivation of metal catalysts in liquid phase organic reactions. Catalysis Today 81, 547 (Jul. 1, 2003).
5. A. I. Abdulagatov et al., Al2O3 and TiO2 Atomic Layer Deposition on Copper for Water Corrosion Resistance. ACS Applied Materials & Interfaces 3, 4593 (2011 Dec. 28, 2011).
6. X. Liang et al., Stabilization of Supported Metal Nanoparticles Using an Ultrathin Porous Shell. ACS Catalysis 1, 1162 (2011 Oct. 7, 2011).
7. R. L. Puurunen, Surface chemistry of atomic layer deposition: A case study for the trimethylaluminum/water process. Journal of Applied Physics 97, 121301 (Jun. 15, 2005).
8. G. C. Chinchen, C. M. Hay, H. D. Vandervell, K. C. Waugh, The measurement of copper surface areas by reactive frontal chromatography. Journal of Catalysis 103, 79 (1//, 1987).
9. K. J. Zeitsch, The chemistry and technology of furfural and its many by-products. Sugar Series (Elsevier, Amsterdam, Netherlands, 2000), vol. 13.
10. E. W. Hagaman et al., Surface alumina species on modified titanium dioxide: A solid-state 27Al MAS and 3QMAS NMR investigation of catalyst supports. Solid State Nuclear Magnetic Resonance 37, 82 (5//, 2010).
11. L. B. Skinner et al., Joint diffraction and modeling approach to the structure of liquid alumina. Physical Review B 87, 024201 (Jan. 3, 2013).
12. J. Greeley, Structural effects on trends in the deposition and dissolution of metal-supported metal adstructures. Electrochimica Acta 55, 5545 (Aug. 1, 2010).
13. J. Lu et al., Porous Alumina Protective Coatings on Palladium Nanoparticles by Self-Poisoned Atomic Layer Deposition. Chemistry of Materials 24, 2047 (2012 Jun. 12, 2012).

14. J. Lu et al., Coking- and Sintering-Resistant Palladium Catalysts Achieved Through Atomic Layer Deposition. *Science* 335, 1205 (2012).
15. C. M. Kim, C. W. Yi, D. W. Goodman, CO—NO and CO—O2 Interactions on Cu(100) between 25 and 200 K Studied with Infrared Reflection Absorption Spectroscopy. *The Journal of Physical Chemistry B* 109, 1891 (2005 Feb. 1, 2005).
16. T. Venkov, K. Hadjiivanov, FTIR study of CO interaction with Cu/TiO2. *Catalysis Communications* 4, 209 (4//, 2003).
17. Q. Sun, J. Xie, T. Zhang, Chemisorption of hydrogen on stepped (410) surfaces of Ni and Cu. *Surface Science* 338, 11 (Sep. 10, 1995).

What is claimed is:

1. A method of performing a heterogeneous catalytic reaction, the method comprising:
   conducting a condensed-phase, heterogeneously catalyzed reaction in the presence of a supported catalyst, wherein the supported catalyst comprises:
   a metal or metal-containing particle supported on a surface; and
   a protective thin film of a material of sufficient thickness to overcoat the metal or metal-containing particle and the surface, thereby yielding an armored surface, wherein the protective surface defines channels that expose a portion of the metal- or metal-containing particle to the surrounding environment; and
   wherein the protective thin film comprises a material selected from the group consisting of $AlO_x$, $HfO_x$, $HfSiO_x$, $LaO_x$, STO, $TaO_x$, $TiO_x$, $ZnO_x$, $ZrO_x$, $WO_x$, $CeO_x$, $MgO_x$, $AlN_x$, $HfN_x$, $SiN_x$, $TaN_x$, $TiN_x$, $AlC_x$, $ZrC_x$, $TiC_x$, $WC_x$, $CeC_x$, and $MgC_x$, wherein subscript "x" is a real, rational number greater than zero.

2. The method of claim 1, wherein the metal or metal-containing particle comprises a base metal or a noble metal.

3. The method of claim 1, wherein the metal or metal-containing particle comprises a base metal.

4. The method of claim 1, wherein the metal or metal-containing particle comprises a metal selected from the group consisting of iron (Fe), nickel (Ni), copper (Cu), zinc (Zn), and lead (Pb).

5. The method of claim 1, wherein the supported catalyst in whose presence the condensed-phase, heterogeneously catalyzed reaction is conducted is produced by a method comprising:
   (a) depositing upon the metal or metal-containing particle supported on the surface via atomic layer deposition or chemical vapor deposition a protective thin film of a material of sufficient thickness to overcoat the metal or metal-containing particle and the surface, thereby yielding an armored surface, wherein the protective thin film has a thickness of from about 1 nm thick to about 100 nm thick; wherein the protective thin film comprises a material selected from the group consisting of $AlO_x$, $HfO_x$, $HfSiO_x$, $LaO_x$, STO, $TaO_x$, $TiO_x$, $ZnO_x$, $ZrO_x$, $WO_x$, $CeO_x$, $MgO_x$, $AlN_x$, $HfN_x$, $SiN_x$, $TaN_x$, $TiN_x$, $AlC_x$, $ZrC_x$, $TiC_x$, $WC_x$, $CeC_x$, and $MgC_x$, wherein subscript "x" is a real, rational number greater than zero; and then
   (b) calcining the armored surface for a time and at a temperature sufficient to form channels in the protective thin film, wherein the channels so formed expose a portion of the metal- or metal-containing particle to the surrounding environment.

6. The method of claim 5, wherein step (a) comprises depositing upon the surface a protective thin film of from about 1 nm thick to about 75 nm thick.

7. The method of claim 5, wherein step (a) comprises depositing upon the surface a protective thin film of from about 1 nm thick to about 50 nm thick.

8. The method of claim 5, wherein step (a) comprises depositing upon the surface a protective thin film of from about 1 nm thick to about 10 nm thick.

9. The method of claim 5, wherein the metal or metal-containing particle comprises a base metal or a noble metal.

10. The method of claim 5, wherein the metal or metal-containing particle comprises a base metal.

11. The method of claim 5, wherein the metal or metal-containing particle comprises a metal selected from the group consisting of iron (Fe), nickel (Ni), copper (Cu), zinc (Zn), and lead (Pb).

* * * * *